United States Patent
Berndt et al.

(10) Patent No.: US 11,633,270 B2
(45) Date of Patent: Apr. 25, 2023

(54) SYSTEMS AND METHODS FOR STERILE DELIVERY OF PROSTHESES

(71) Applicant: RTRS INVESTMENT, LLC, Dallas, TX (US)

(72) Inventors: Ernst-Ulrich Gerhard Berndt, Berlin (DE); Ruedger Rubbert, Berlin (DE); Andreas Weinrich, Berlin (DE); Jonathan Cornelius Berndt, Berlin (DE); Sabine Schulz, Berlin (DE)

(73) Assignee: RTRS Investment, LLC, Dallas, TX (US)

( * ) Notice: Subject to any disclaimer, the term of this patent is extended or adjusted under 35 U.S.C. 154(b) by 0 days.

(21) Appl. No.: 15/153,598

(22) Filed: May 12, 2016

(65) Prior Publication Data

US 2016/0361146 A1    Dec. 15, 2016

Related U.S. Application Data

(60) Provisional application No. 62/174,895, filed on Jun. 12, 2015.

(51) Int. Cl.
*A61C 19/02* (2006.01)
*A61C 8/00* (2006.01)
(Continued)

(52) U.S. Cl.
CPC .............. *A61C 19/02* (2013.01); *A61C 8/0087* (2013.01); *A61F 2/0095* (2013.01); *B65B 7/16* (2013.01);
(Continued)

(58) Field of Classification Search
CPC .............. A61C 19/02; A61C 8/0087; A61C 2202/00; A61F 2/095; B65F 7/16
See application file for complete search history.

(56) References Cited

U.S. PATENT DOCUMENTS

| | | | | |
|---|---|---|---|---|
| 4,614,008 A | * | 9/1986 | Brill | D06F 55/02 24/501 |
| 4,801,015 A | * | 1/1989 | Lubock | A61F 2/2427 206/525 |

(Continued)

FOREIGN PATENT DOCUMENTS

| | | |
|---|---|---|
| EP | 2754410 A1 | 7/2014 |
| KR | 20090009102 | 9/2009 |

(Continued)

OTHER PUBLICATIONS

International Search Report and Written Opinion dated Sep. 29, 2016 for corresponding International Application No. PCT/EP2016/062974.

(Continued)

*Primary Examiner* — Yogesh P Patel
(74) *Attorney, Agent, or Firm* — Polsinelli PC

(57) ABSTRACT

Systems and methods are disclosed for sterile delivery of prostheses that protect refined and/or conditioned surface properties and thereby reduce aging of surface properties in prostheses. An example of the system includes a partially custom-shaped holder that also serves as an insertion tool that holds a customized dental prosthesis in a pre-defined position inside a titanium container that is hermetically sealed. Container materials serve as a getter or catalyst with respect to the osseoconductive surface. An example of the method includes laser welding to hermetically seal a metal container as packaging for a prosthesis with a metal foil, and the sterilization of the packaged and sealed prosthesis with dry heat.

16 Claims, 20 Drawing Sheets

(51) Int. Cl.
*A61F 2/00* (2006.01)
*B65B 7/16* (2006.01)
*B65B 51/22* (2006.01)
*B65B 55/06* (2006.01)
*B65D 6/02* (2006.01)
*B65D 6/04* (2006.01)
*B65D 17/50* (2006.01)
*B65D 25/10* (2006.01)

(52) U.S. Cl.
CPC .............. *B65B 51/22* (2013.01); *B65B 55/06* (2013.01); *B65D 7/06* (2013.01); *B65D 7/08* (2013.01); *B65D 17/501* (2013.01); *B65D 25/10* (2013.01); *A61C 2202/00* (2013.01)

(56) References Cited

U.S. PATENT DOCUMENTS

| | | | | |
|---|---|---|---|---|
| 4,945,613 | A * | 8/1990 | Ledermann | D06F 55/02 24/501 |
| 5,236,450 | A * | 8/1993 | Scott | A61F 2/2427 623/2.11 |
| 5,720,391 | A * | 2/1998 | Dohm | A61F 2/0095 206/583 |
| 6,702,855 | B1 | 3/2004 | Steinemann et al. | |
| 2005/0035015 | A1 | 2/2005 | Bressler et al. | |
| 2007/0181446 | A1 | 8/2007 | Donahoe et al. | |
| 2007/0209957 | A1 | 9/2007 | Glenn et al. | |
| 2010/0133124 | A1 | 6/2010 | Satoh et al. | |
| 2011/0143315 | A1 * | 6/2011 | Guenter | A61C 8/0089 433/147 |
| 2013/0299371 | A1 * | 11/2013 | Johansson | A61C 19/02 206/349 |
| 2014/0080093 | A1 | 3/2014 | Rubbert | |
| 2014/0087327 | A1 * | 3/2014 | Noack | A61C 13/0022 433/50 |

FOREIGN PATENT DOCUMENTS

| | | |
|---|---|---|
| KR | 20100034372 | 4/2010 |
| WO | 2010058254 A1 | 5/2010 |
| WO | 2011113568 A1 | 9/2011 |
| WO | WO2021026051 A1 * | 11/2021 |

OTHER PUBLICATIONS

International Search Report and Written Opinion dated Oct. 24, 2016 for corresponding International Application No. PCT/EP2016/062978.
English Translation of KR 20090009102.
English Translation of KR 20100034372.

* cited by examiner

0301

0305

0302

0308

0304

17A: Surface Conditioning of Prosthesis

17B: Clamp Prosthesis with Holder Components

17C: Insert Holder in Container

17D: Seal Container

17E: Sterilize Packaged Prosthesis

17F: Heat Activate Surface inside Container

17G: UV Activate Surface inside Container

17H: Open Container for Sterile Delivery

17I: Use Holder to Place Prosthesis Clinically

Fig. 17

```
18A: Customize Prosthesis
          │
18B: Surface Conditioning of Prosthesis
          │
18C: Customize Holder Components
          │
18D: Clamp Prosthesis with Holder Components
          │
18E: Insert Holder with Prosthesis in Container
          │
18F: Seal Metal Container with Metal Foil
     Hermetically by Laser Welding
          │
18G: Sterilize Sealed Container with Dry Heat
          │
18H: Open Container for Sterile Delivery
          │
18I: Use Holder to Place Prosthesis Clinically
```

Fig. 18

SYSTEMS AND METHODS FOR STERILE DELIVERY OF PROSTHESES

PRIORITY

The present application is a non-provisional patent application of and claims benefit to and the priority of U.S. Prov. App. No. 62/174,895, filed Jun. 12, 2015, the entire disclosure of which is hereby expressly incorporated herein by reference.

BACKGROUND OF THE INVENTION

Field of the Invention

The present invention relates generally to the field of implantology, and more particularly to the field of dental restorations, implants and prostheses. The present invention further relates to packaging, surface refinement and sterilization of medical devices in general.

Description of Related Art

The individual, partial or full CAD/CAM-based customization of prostheses is a modern trend towards further individualized patient-specific life science and health care services. U.S. patent application Ser. No. 14/086,537 to Rubbert (published as U.S. Pub. No. 2014/0080093), which is incorporated herein by reference in its entirety, describes in an exemplary embodiment a fully customized dental prosthesis that mimics the three-dimensional shape of a non-functional tooth, derived from three-dimensional imagining data, adjusted for straight insertion, that provides an anatomically shaped emerging profile, and that comprises a custom-shaped prosthetic post to receive a crown and is intended to be placed in the alveolar socket directly after the extraction of the non-functional tooth. Rubbert describes in the aforementioned '537 application various surface conditionings to either enhance osseointegration over fibrous encapsulation or to promote the regeneration of the periodontal ligament.

Packaging solutions for implants are required to avoid or at least minimize any contact between the implant's surface and the packaging materials during transportation, so that the materials of the packaging do not damage or alter the implant, for example by the packaging contacting the implant's surfaces, and rubbing off portions of the surface or by otherwise contaminating the implant surfaces. Sterilization of packaged products is the generally accepted standard for medical devices, and implants in particular. The packaging provides a sterile barrier that maintains sterilization during transportation and shelf life. Sterilization with moist heat, or other toxic gases, requires semi-permeable packaging components so that the sterilization agent is able to infiltrate and saturate the packaging volume and reach at least the surfaces of the medical device, or implant, in order to provide the level of bacterial overkill required by law or regulatory bodies. Volumetric sterilization methods like gamma radiation may damage or deteriorate material properties and cannot be used for certain medical devices.

Environmental air surrounding a medical device or implant, including fumes, pollution, and gas components that evaporate from packaging materials contaminate refined surfaces of medical devices within packaging containers. Purified surfaces "age" within hours and days being exposed to environmental air, so that, for example hydrocarbons are spreading out in cumulating molecular layers on implant surfaces, turning clean and refined hydrophilic surfaces, available directly after manufacturing processes, for example after etching of endosseous implant surfaces, into hydrophobic surface properties. The initial immediate and direct contact between refined implant surfaces and blood proteins is considered to enhance the hard and soft tissue integration. Hydrophobic surfaces and surfaces contaminated with hydrocarbons, for example from packaging emissions, are considered detrimental to that enhancement.

Steinemann et al. describe in U.S. Pat. No. 6,702,855, which is incorporated herein by reference in its entirety, an implant having improved osseointegration characteristics. The implant consists of titanium or a titanium alloy. The implant is provided with a rough "hydroxylated and hydrophilic surface which is at least sealed in a gastight and liquid-tight covering. The interior of said covering is provided with an inert atmosphere, preferably consisting of nitrogen, oxygen and/or inert gas and/or is at least partially filled with purified water," which optionally contains additives.

SUMMARY OF THE INVENTION

All described options and methodologies are deficient and/or limited in their respective scope. There has not been recognition, until now by the inventors, of the need for systems, and related methods that include, for example, an at least partially custom-shaped holder to clamp or otherwise fixate a custom-shaped prosthesis in a packaging container to avoid any contact between the implant surface(s) conditioned for tissue integration with the surrounding packaging materials, wherein the holder may or may not also be used as an insertion tool. Methods include hermetically sealing a metal container with a metal foil that serves as a packaging component to protect refined, purified or otherwise conditioned surfaces of prostheses against environmental air. Further methods include sterilizing the prostheses inside the hermetically sealed container, for example by means of gamma radiation or dry heat.

In some systems and methods, for example, titanium is used for the container and the foil, for example with desorbed and/or conditioned surfaces that serve as getter and/or catalyst to clean at least the air inside the hermetically sealed container, the getter, for example, being further activated by heat treatment. In other systems and methods, integrated light emitting diodes (LEDs) or optical windows are utilized with and/or disposed within the container, so that the implant surfaces can be treated with ultraviolet A (UVA) and/or ultraviolet B (UVB) light activated inside the hermetically sealed container. All of the foregoing components and steps, alone or in any combination, can be used to protect refined implant surfaces during sterilization, transportation and shelf-life and/or to enable appropriate fixation and handling of customized prostheses for sterile delivery and insertion, so that the gain in surface purity and in handling accuracy enhances hard or soft tissue integration of implant surfaces of prostheses and reduces surgical errors.

There is also no prior recognition of the tooling required to laser weld a foil onto a container surface in the context of packaging medical devices, or implants, in order to account for tolerances in the evenness or levelness, and equality of height of the surfaces to be welded and dimensions of the container, so that more controlled and more robust manufacturing technologies ease dimensional production tolerances and thereby gain efficiencies.

The system(s) and method(s) provided by the various embodiments of the present disclosure comprise several independent inventive features providing substantial improvements. Benefits will be achieved in the field of implantology, and more particularly in the field of dental restorations, implants and prostheses and in the area of packaging, surface refinement and sterilization of medical devices in general.

One objective of the present invention is to provide a solution for safely packaging and storing a medical device in general, or a prosthesis or a dental implant in particular. For example, a surface conditioning has been performed to ensure that a dental implant supports either osseointegration over fibrous encapsulation, or promotes the regeneration of the periodontal ligament. In order to preserve and maintain those surface properties, the packaging must shield and protect the implant from external influences; the implant is to remain fully shielded inside a packaging container or covering until sterile clinical delivery of the implant, including its implantation, and actual use.

Another aspect is to prevent the implant from coming into contact with the packaging materials in order to prohibit the implant from rubbing against the encasement. Accordingly, the implant, custom-shaped or of generic shape, must be fixed inside the packaging container so that any movement relative to the envelope of the encasement is prevented, even under rough conditions to be expected during transportation and handling.

A further objective of the present invention is to allow reliable and easy removal of the implant from the package by the dentist or surgeon or an assistant prior to the implantation process. In order to support osseointegration or regeneration of the periodontal ligament, it is desirable that the tissue-integrating or anchoring portion of the implant can remain completely untouched during removal and insertion into the tissue of the patient. In addition, the process of removing the implant from the package, and placing it into the body cavity considering the proper orientation should not present any challenges requiring undue carefulness.

In an exemplary embodiment of the invention, the implant is mechanically fixed inside the packaging container using an interlocking, positive fit or form closure system. A holder or two or more holders are shaped so that they partially embrace the implant. Depending on the nature of the implant, they can be customized to precisely match the shape of the implant, and can even be shaped under consideration of the teeth adjacent to the implant.

The holders can be firmly connected to the packaging container, and locked in place, but are removable, so that the implant can be removed from the container together with the holders. In another exemplary embodiment of the present invention, the holders are shaped so that they can be used to remove the implant from the container, and thereafter to handle the implant and place it in the right orientation and position into the body cavity, thus, in some cases, avoiding the need for further tools or manipulation means.

This embodiment preferably would comprise two holders shaped according to the implant, and connecting to the implant by an interlocking, positive fit, form closure or clamping mechanism, or a combination thereof After having placed the implant properly, the holders are to be released from the implant. In one embodiment, this can be performed without applying considerable force onto the prosthesis.

In order to support the correct rotational orientation, for example, of a dental implant, in another embodiment of the invention, the holders are equipped with at least one marker identifying the pre-defined position, for example a vestibular portion of the dental implant. The marker of the holder of a prosthesis may correlate with a respective marker placed on the prosthesis.

A packaging container is made from a material supporting the preservation of the refined and/or conditioned surfaces of the prosthesis. Specialty implants are manufactured with a broad spectrum of surface conditioning processes to support and enhance osseointegration over fibrous encapsulation or to promote the regeneration of the periodontal ligaments, or the integration with soft tissues in general. The aforementioned '537 application describes a great variety of possible surface conditioning, and it is essential that the surface properties achieved by those or other treatments are preserved to the maximum extent during the shipping and delivery process.

In an exemplary embodiment, a casing made from titanium is used. The inner surface of a titanium casing would also serve as getter or catalyst to attract and retain or dissolve any residual contamination. The inner surfaces, or portions thereof, may be surface treated to improve the getter feature, for example by desorption, sandblasting, etching, coating, and plasma cleaning, or any combination thereof in order to increase the surface, for example, by increasing the surface roughness, and/or to remove residual contamination. As used herein, the term "getter" refers to a substance, such as, for example, titanium disposed in a vessel, optionally under a vacuum, to adsorb residual gas in the vessel. In some embodiments, the getter further acts as a catalyst allowing for a reaction of the residual gas, the residual gas being adsorbed to the surface of the getter and/or dissolved, e.g., breaking up hydrocarbons by a catalytic process.

Additional, optional means are provided to further improve the purity of the inside of the casing. One such means includes, for example, a thin sheet having a meandering shape enclosed within in the container. This sheet provides a significant enlargement of the inner surface serving as a getter medium. In another embodiment, LEDs emitting ultraviolet light are mounted inside the casing, providing radiation suitable for breaking up hydrocarbons, and for changing the electro-static charge of the surface (which is reported to be conductive to cell attachment and cell propagation) when activated. In yet another embodiment, portions of the casing are made from quartz glass, allowing the implant or prosthesis to be exposed to ultraviolet radiation through the sealed covering or encasement at any point in time.

In order to maintain the purity of the inside of the casing after the implant and the holders have been inserted, the container must be sealed hermetically. In an exemplary embodiment, the casing is made from titanium, and a foil made from the same material is welded directly to the casing, thus closing the opening, and creating a robust and hermetically tight enclosure. During the welding process, the foil must be pressed tight against the casing in order to avoid leakage or cracks. For example vacuum, inert gas, or purified air may further enhance the environment inside the hermetically sealed covering of a prosthesis or implant.

Disclosed herein is a container for protectively holding a prosthesis for storage and transport. The container includes a casing; a sealing foil, wherein the sealing foil encloses an open portion of the casing, and wherein the sealing foil comprises an inner surface facing the prosthesis; and a holder, wherein the holder grips a portion of the prosthesis, wherein the holder is operable to support the prosthesis within the casing, and wherein the holder is operable to prevent contact between the prosthesis, an inner surface of the casing, and the inner surface of the sealing foil. In some embodiments, the inner surface of the casing is operable to reduce impurities within the container that negatively impact the prosthesis. In other embodiments, the container further includes an insert disposed between the holder and the casing, wherein the insert is operable to reduce impurities within the container that negatively impact the prosthesis.

Still in other embodiments, the holder comprises a first clamp and a second clamp, wherein the clamps are joined by a hinge. In certain embodiments, the holder further comprises a specialty manufactured portion correspondingly formed to hold a specialty manufactured prosthesis. Still in other embodiments, the specialty manufactured prosthesis is a dental implant. In yet other embodiments, the container further comprises at least one material selected from the group consisting of: titanium, titanium alloy, active carbon, a metal oxide, and zeolite-like materials. In some embodiments, the sealing foil is hermetically sealed to the casing. In certain embodiments, the holder is removable by hand and operable to insert the prosthesis into a patient's body without the prosthesis being removed from the holder prior to insertion into the patient's body.

In some embodiments of the container, the insert is flexibly positioned for insertion of the holder into the insert. In other embodiments, an outer surface of the holder is specially manufactured for insertion of the prosthesis into the patient's body between existing portions of the patient's body. In certain embodiments, the container is under a vacuum once the foil is hermetically sealed to the casing. Still in other embodiments of the container, the casing includes a meandering-shaped getter surface for reducing impurities within the container that negatively impact the prosthesis. In some embodiments, the casing includes light-emitting sources operable to emit UV light toward the prosthesis. Still in yet other embodiments, the casing includes transparent portions operable to allow UV light to travel through the casing toward an interior of the container and the prosthesis.

Additionally disclosed herein is a method for seamless prosthesis design and transport. The method includes the steps of: shaping a prosthesis according to a specific patient's anatomical features; conditioning the surface of the prosthesis for healthy integration of the prosthesis into the patient's body; inserting the prosthesis within a container for protectively holding a prosthesis for storage and transport, the container comprising: a casing, wherein the casing comprises an inner surface operable to reduce impurities within the container that negatively impact the prosthesis; and a holder, wherein the holder grips a portion of the prosthesis, wherein the holder is operable to support the prosthesis within the casing, and wherein the holder is operable to prevent contact between the prosthesis and the inner surface of the casing; and hermetically sealing the container.

In some embodiments of the method, the step of hermetically sealing the container further comprises the step of utilizing a sealing foil, wherein the sealing foil encloses an open portion of the casing, wherein the sealing foil comprises an inner surface facing the prosthesis, and wherein the holder is operable to prevent contact between the prosthesis and the inner surface of the sealing foil. In some embodiments, the method further comprises the step of heat activating an inner surface of the container. In some embodiments, the method further comprises the step of activating a surface of the prosthesis with UV light. In some embodiments, the method further comprises the step of opening the container for sterile delivery.

In some embodiments, the method further includes the step of using the holder to place the prosthesis clinically in a patient while preventing any human contact with the prosthesis, other than that of a patient.

Additionally disclosed is a system for protectively packaging a prosthesis, the system including an encasement; a prosthesis including a first custom-shaped portion; and a holder including a second custom-shaped portion, the first custom-shaped portion and the second custom-shaped portion provide a form-locking interface, so that, when the holder is operationally positioned inside the encasement and when the prosthesis is operationally positioned in the holder, the holder fixates the prosthesis by means of the form-locking fit in a pre-defined position and orientation inside the encasement. In some embodiments of the system, the prosthesis is a dental implant. Still in other embodiments of the system, the holder comprises a first clamp and a second clamp, the first clamp and the second clamp configured to provide a clamping mechanism, the holder being operable to position the prosthesis in the holder and release the prosthesis from the holder.

Still in other embodiments of the system, the prosthesis comprises an at least partially custom-shaped preparation post to receive a dental crown and a surface of the preparation post is at least a portion of the first custom-shaped portion. In certain embodiments, the second custom-shaped portion at least partially includes an inverse shape of the preparation post that substantially matches a corresponding portion of the preparation post of the dental implant.

Additionally disclosed is a system for sterile delivery and controlled handling of a prosthesis. The system includes a prosthesis including a first custom-shaped portion; a holder including a second custom-shaped portion, the first custom-shaped portion and the second custom-shaped portion provide a form-locking interface, so that, when the prosthesis is operationally positioned in the holder, the holder fixates the prosthesis by means of the form-locking fit in a pre-defined position and orientation with respect to the orientation and position of the holder. In some embodiments, the prosthesis is a dental implant. Still in other embodiments, the holder comprises a first clamp and a second clamp, the first clamp and the second clamp are configured to provide a clamping mechanism, so that a user that operationally positions the prosthesis in the holder is enabled to clamp the dental implant or to release the prosthesis from the holder.

In some embodiments, the prosthesis comprises an at least partially custom-shaped preparation post to receive a dental crown and a surface of the preparation post is at least a portion of the first custom-shaped portion. Still in other embodiments, the second custom-shaped portion at least partially includes an inverse shape of the preparation post that substantially matches a corresponding portion of the preparation post of the dental implant.

Additionally disclosed is a holder for holding a prosthesis, and the holder includes a custom-shaped holder portion that grips a custom-shaped portion of the prosthesis. In some embodiments, the holder is operable to grip the prosthesis in a predefined spatial position and orientation with respect to a spatial position and orientation of the holder. In certain embodiments, the holder comprises a first clamp and a second clamp, wherein the clamps are joined by a hinge. In certain embodiments, the holder comprises a first clamp and a second clamp, the first clamp and the second clamp configured to provide a clamping mechanism, the holder being operable to position the prosthesis in the holder and release the prosthesis from the holder.

Still in other embodiments, the first clamp includes a first custom-shaped inverse portion, wherein the first custom-shaped inverse portion is the custom-shaped holder portion, wherein the second clamp includes a second custom-shaped inverse portion, and the first custom-shaped inverse portion and the second custom-shaped inverse portion provide a form-locking interface with the custom-shaped portion of the prosthesis, so that, when the prosthesis is positioned in the holder, the form-locking interface fixates the prosthesis in the holder. In certain embodiments, the holder is operable to insert the prosthesis into a patient's body without the prosthesis being removed from the holder prior to insertion into the patient's body.

In still yet other embodiments, the custom-shaped holder portion includes a key feature providing an undercut that provides an interlock with a corresponding inverse feature of the custom-shaped portion of the prosthesis when the prosthesis is positioned in the holder. In still other embodiments, the holder includes a mark allowing a user to handle and insert the prosthesis in a correct orientation in a location in which a correct orientation is necessary for insertion of the prosthesis. Still in yet other embodiments, an outer surface of the holder includes a custom-shaped outer portion operable to enable the insertion of the prosthesis into the patient's body between existing portions of the patient's body.

In some embodiments, the prosthesis is a custom-made dental implant. In other embodiments, the holder includes a mark, marking the vestibular side of the dental implant. In certain embodiments, the custom-made dental implant comprises an at least partially custom-shaped preparation post to receive a dental crown and a surface of the preparation post is the custom-shaped portion of the prosthesis. Still in other embodiments, the custom-shaped portion of the holder at least partially includes an inverse shape of the preparation post that substantially matches a corresponding portion of the custom-shaped portion of the preparation post of the dental implant. In some embodiments, the holder comprises zirconia. Still in yet other embodiments, the holder comprises titanium.

Additionally disclosed is a system for providing a holding mechanism for a prosthesis. The system includes a first data set representing the three-dimensional shape of a custom-shaped portion of the prosthesis, and a holder having a first custom-shaped portion operable to hold the prosthesis. In some embodiments of the system, the holder is operable to insert the prosthesis into a patient's body without the prosthesis being removed from the holder prior to insertion into the patient's body. Still in other embodiments of the system, an outer surface of the holder includes a custom-shaped outer portion operable to enable the insertion of the prosthesis into the patient's body between existing portions of the patient's body.

In certain embodiments, the first custom-shaped portion of the holder at least partially correlates to the three-dimensional shape of the custom-shaped portion of the prosthesis as represented by the first data set. In certain embodiments, the holder includes a second custom-shaped portion, wherein the prosthesis is a dental implant to replace a pre-identified tooth of a specific patient, and wherein the system further comprises: a second data set representing a three-dimensional crown shape of a tooth adjacent to the pre-identified tooth of the specific patient. Still in other embodiments, the second custom-shaped portion at least partially correlates to the three-dimensional crown shape as represented by the second data set.

In yet other embodiments, the dental implant comprises a custom-shaped single-root portion. In some embodiments, the dental implant comprises a custom-shaped multi-root portion.

Additionally disclosed is a method for design and manufacturing of a holder, the holder operable to fixate a prosthesis, the method including the steps of: receiving a first shape data set representing a three-dimensional shape of a custom-shaped portion of the prosthesis; deriving a first manufacturing data set of a first virtual custom-shape from the first shape data set; and shaping at least a first custom-shaped portion of the holder responsive to the first manufacturing data set. In some embodiments of the method, the method step of deriving the first manufacturing data set utilizes a Boolean algorithm. In certain embodiments of the method, the method step of shaping utilizes a rapid prototyping technology. In some embodiments, the method step of shaping utilizes a numerical controlled milling technology. Still in other embodiments, the holder is made of zirconia, and the method further comprises the step of sintering the holder.

In some embodiments of the method, the method further includes the step of sterilizing the holder. Still in other embodiments, the prosthesis is a custom-made dental implant operable to replace a pre-identified tooth of a specific patient, and wherein the method further includes the steps of: receiving a second shape data set representing a three-dimensional shape of a crown of a tooth adjacent the pre-identified tooth to be replaced by the custom-made dental implant; deriving a second manufacturing data set of a second virtual custom-shape from the second data set; and shaping at least a second custom-shaped portion of the holder responsive to the second manufacturing data set.

In certain embodiments, the method step of deriving the second manufacturing data set utilizes a Boolean algorithm. In other embodiments, the holder comprises a first clamp and a second clamp, the first clamp and the second clamp configured to provide a clamping mechanism to fixate the prosthesis. Still in other embodiments, the method further includes the step of making a mark into or onto the holder in correlation to a specific orientation of the prosthesis, the mark visible when the holder fixates to the prosthesis. In yet other embodiments of the method, the method step of making a mark includes a shaping process, and wherein the mark is a notch shaped into the holder. Still in other embodiments, the prosthesis is a custom-shaped dental implant and the mark indicates the vestibular side of the custom-shaped dental implant, when the prosthesis is positioned in the holder.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 17 shows a flow chart of process steps for one embodiment of a method of the present invention.

FIG. 18 shows a flow chart of process steps for one embodiment of a method of the present invention.

FIG. 20a shows a partially cross-sectional view of an exemplary modification of the tool components shown in FIG. 19, the modification allowing a user to fixate a casing and a foil in very close proximity to each other, compensating for dimensional variances in the evenness or levelness of the surface of the casing to which the foil is being welded, in accordance with an embodiment of the present invention.

FIG. 20b shows a partially cross-sectional close up of details of the tool components shown in FIG. 20a.

DETAILED DESCRIPTION

The present invention will now be described more fully hereinafter with reference to the accompanying drawings, which illustrate embodiments of the present invention. This invention may, however, be embodied in many different forms and should not be construed as limited to the illustrated embodiments set forth herein. Rather, these embodiments are provided so that this disclosure will be thorough and complete, and will fully convey the scope of the present invention to those skilled in the art. Like numbers refer to like elements throughout. The different numbering of identical or similar components and/or prime notation, if used, indicates similar elements in alternative embodiments and/or configurations.

Figure 1:
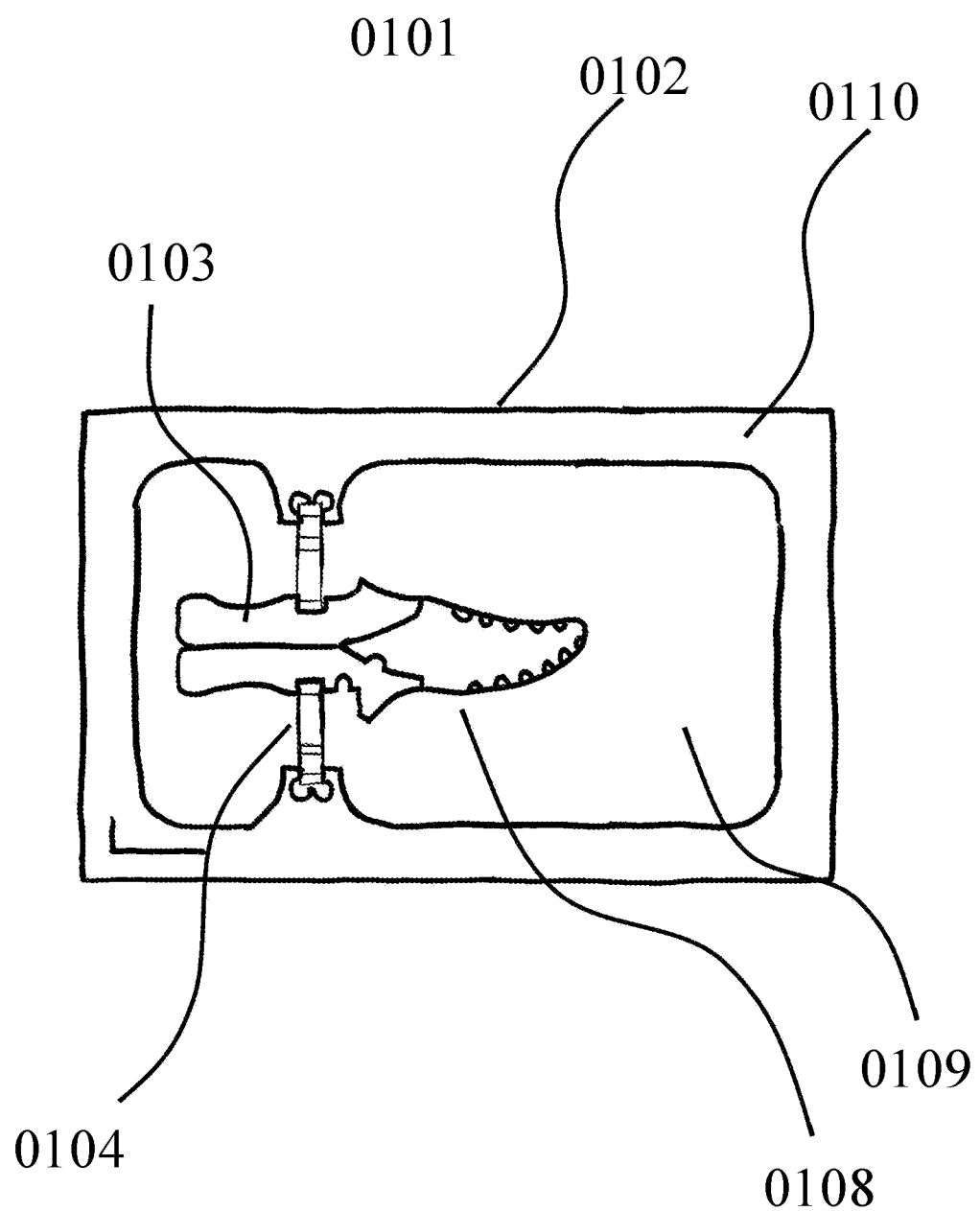
FIG. 1 shows a top view of a packaging container having a custom-shaped, single-rooted root-analogue dental implant disposed within the packaging container, in accordance with an embodiment of the present invention.

FIG. 1 shows the top view of a packaging container (0101), the container (0101) comprising a casing (0102), made from metal like titanium or a titanium alloy, including a custom-shaped, single-rooted, root-analogue dental implant (0108) disposed within packaging container (0101) by two holders (0103) and a flat-sheet material insert (0104). One purpose of inserts (0104) is to connect the holders (0103) to the casing (0102), and thus ensure a safe and motion-free positioning of the implant (0108) inside the container (0101). In an exemplary embodiment, the casing (0102) is made from one piece, consisting of a bottom plate (0109) and walls (0110).

The casing shown in FIG. 1 is milled. In another embodiment, the casing is produced using selective laser melting, or similar methods. Selective laser melting will produce a rough surface compared to milling, which improves the getter properties of the casing. If a sheet metal is to be welded to the casing to enclose the container (optionally hermetically seal the container), the side of the casing facing the sheet metal may by grinded or milled in order to receive a smooth surface.

In another embodiment, conventional laboratory or industrial procedures such as, for example, casting are used to manufacture the casing and container. Other options include rapid-prototyping methods like high-speed milling or high-speed grinding.

Figure 15:
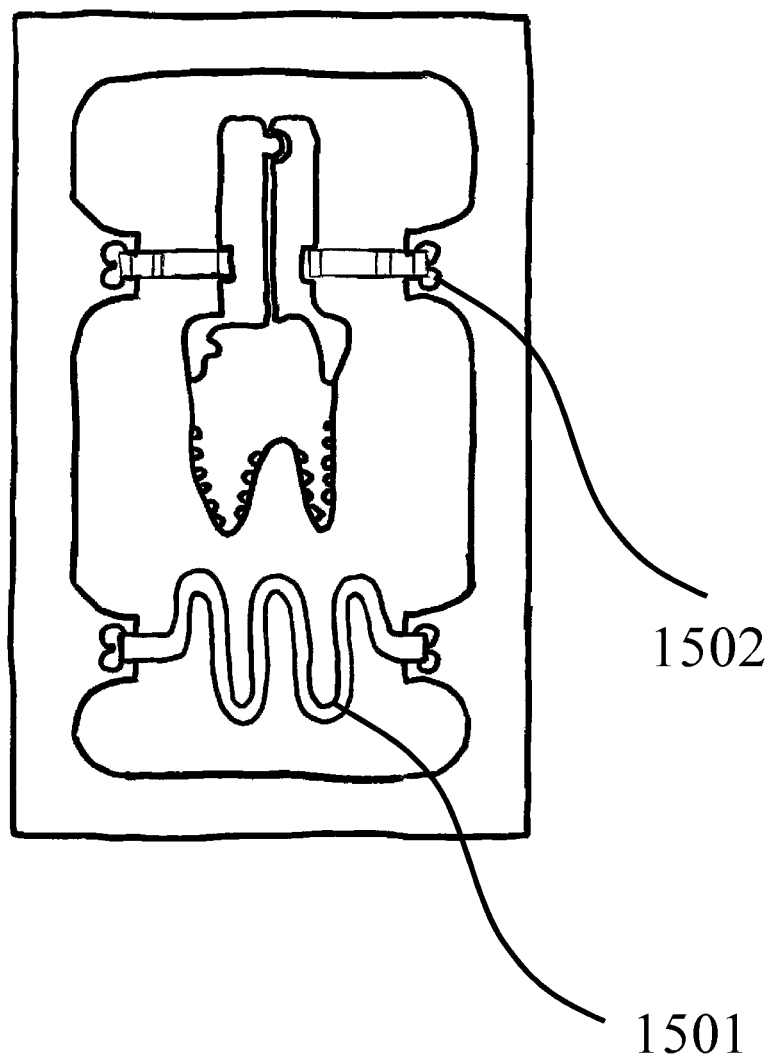
FIG. 15 shows a top view of the packaging container having a custom-shaped, multi-rooted, root-analogue dental implant disposed within the packaging container, and having an additional meandering flat sheet material that serves as an additional getter surface in accordance with an embodiment of the present invention.

In yet another embodiment, for example a ceramic material is used for the casing and/or container, and additional sheets of titanium or another suitable material are placed into the casing to serve as getter medium, as illustrated in FIG. 15. The getter medium can be fixed to the container for example by screws, or welding, or it can be shaped so that it will be held in place by slots and/or protrusions present in the container/casing, or it would show a degree of flexibility so that it can be secured inside the container by frictional forces, or a combination thereof. Depending on the material of the prosthesis, the getter material could be, for example, at least one of, or any combination of, the following: titanium, titanium alloy, other metals, other metallic alloys, active carbon, metal oxides, zeolite-like materials, and other non-metallic substances. The getter material could consist, for example, of at least one of the following: coatings, flat sheet material, granules, powder, solid bodies, and spongy-like bodies.

Preferably, at least the customized portion of the packaging container is fabricated using a CAD/CAM based method and system. In another exemplary embodiment, more than one prosthesis, or several parts of a medical device are placed and fixated inside the packaging container, for example a dental implant, a temporary cantilever bridge and an accessory to the dental implant, such as a test body to check the integrity of the insertion path prior to using the dental implant.

Figure 2:
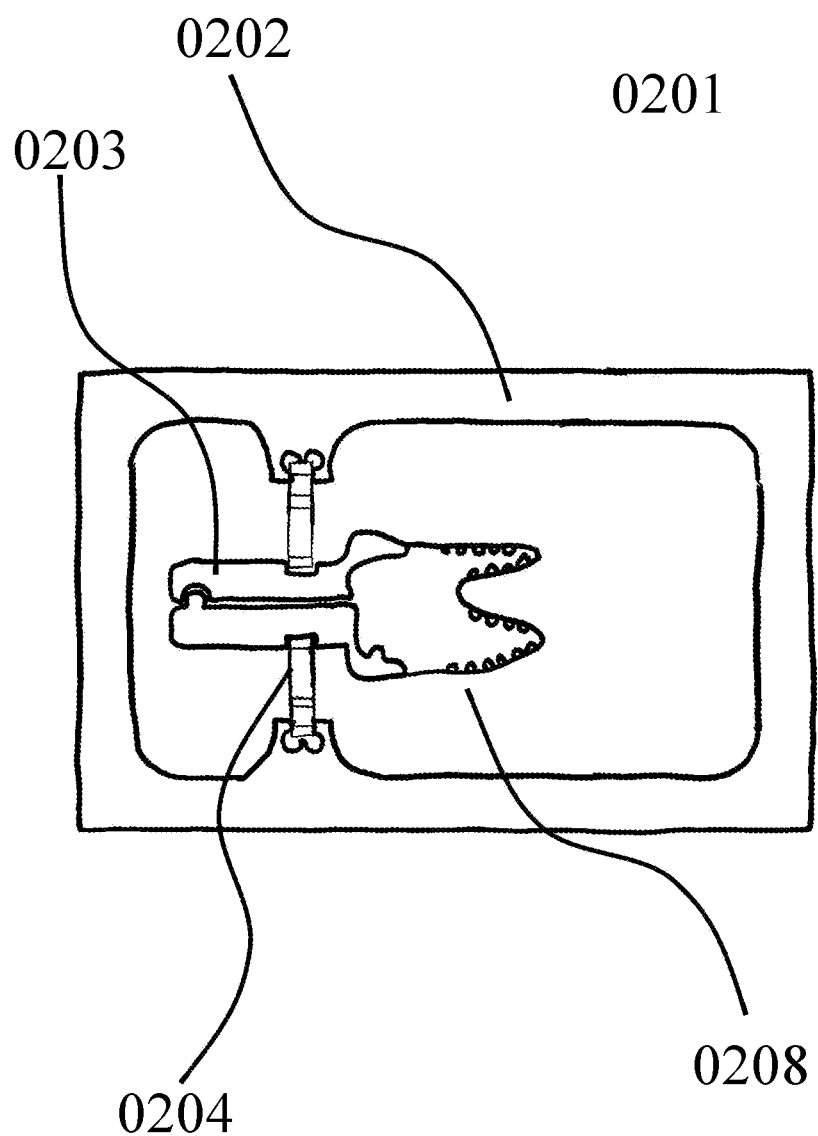
FIG. 2 shows a top view of a packaging container having a custom-shaped, multi-rooted, root-analogue dental implant disposed within the packaging container, in accordance with an embodiment of the present invention.

FIG. 2 shows a packaging container (0201) including a casing (0202), a custom-shaped, multi-rooted, root-analogue dental implant (0208), together with two holders (0203), and a flat sheet material insert (0204).

Figure 3:
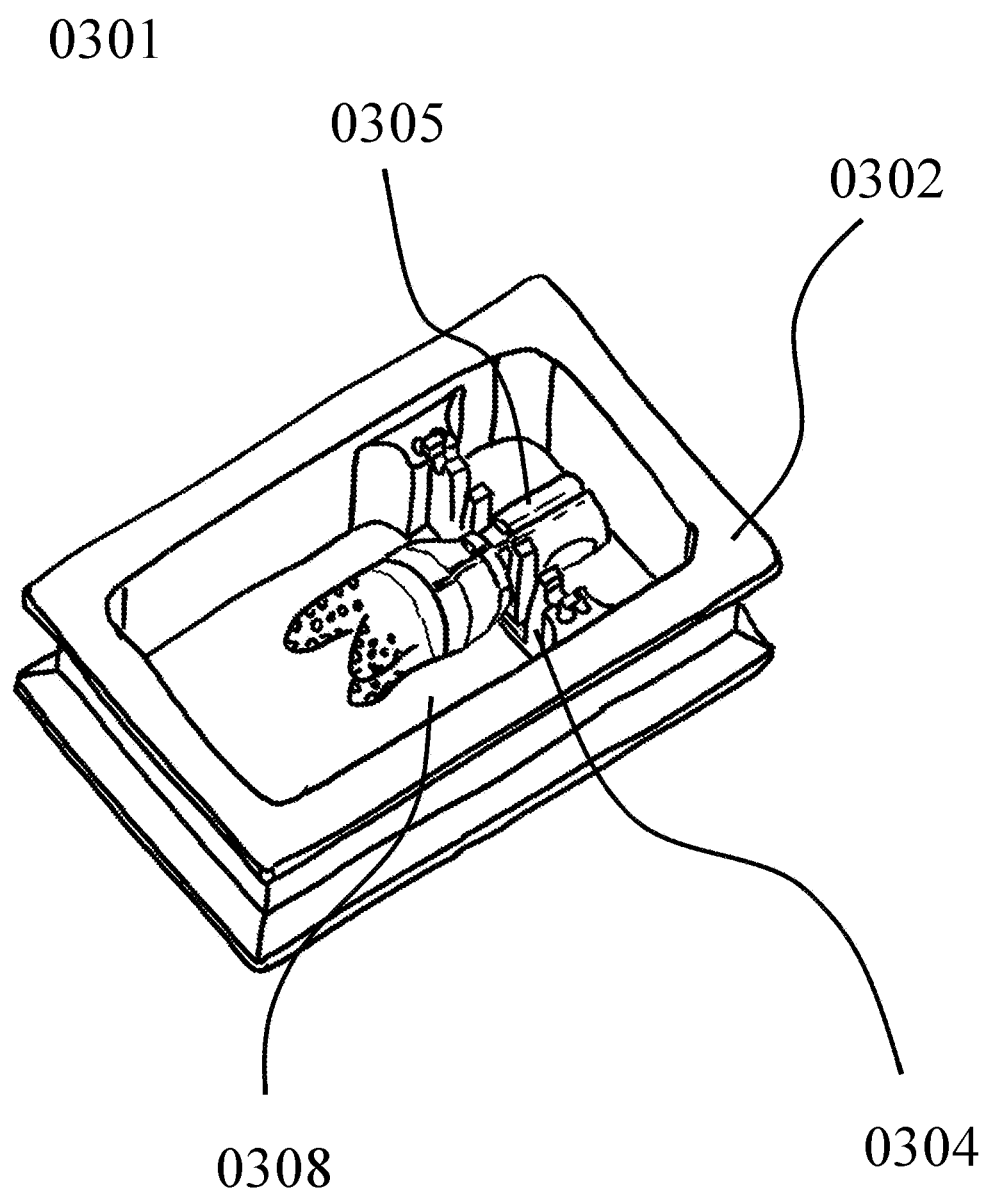
FIG. 3 shows a perspective view of the packaging container of FIG. 2.

FIG. 3 shows a packaging container (0301) including a casing (0302), a custom-shaped, multi-rooted, root-analogue dental implant (0308) together with two holders (0305), and a flat sheet material insert (0304). FIG. 3 illustrates an embodiment of a casing in a three-dimensional (3D) view. This view also shows an example of inserts (0304), serving as connector between the holders (0305) and the casing (0302). In example embodiments, an insert can be a single monolithic piece, such as a single piece of sheet metal, or the insert can be designed from multiple, connected pieces or parts. In example embodiments, there can be one insert in a casing, or multiple inserts in a casing.

Figure 4:
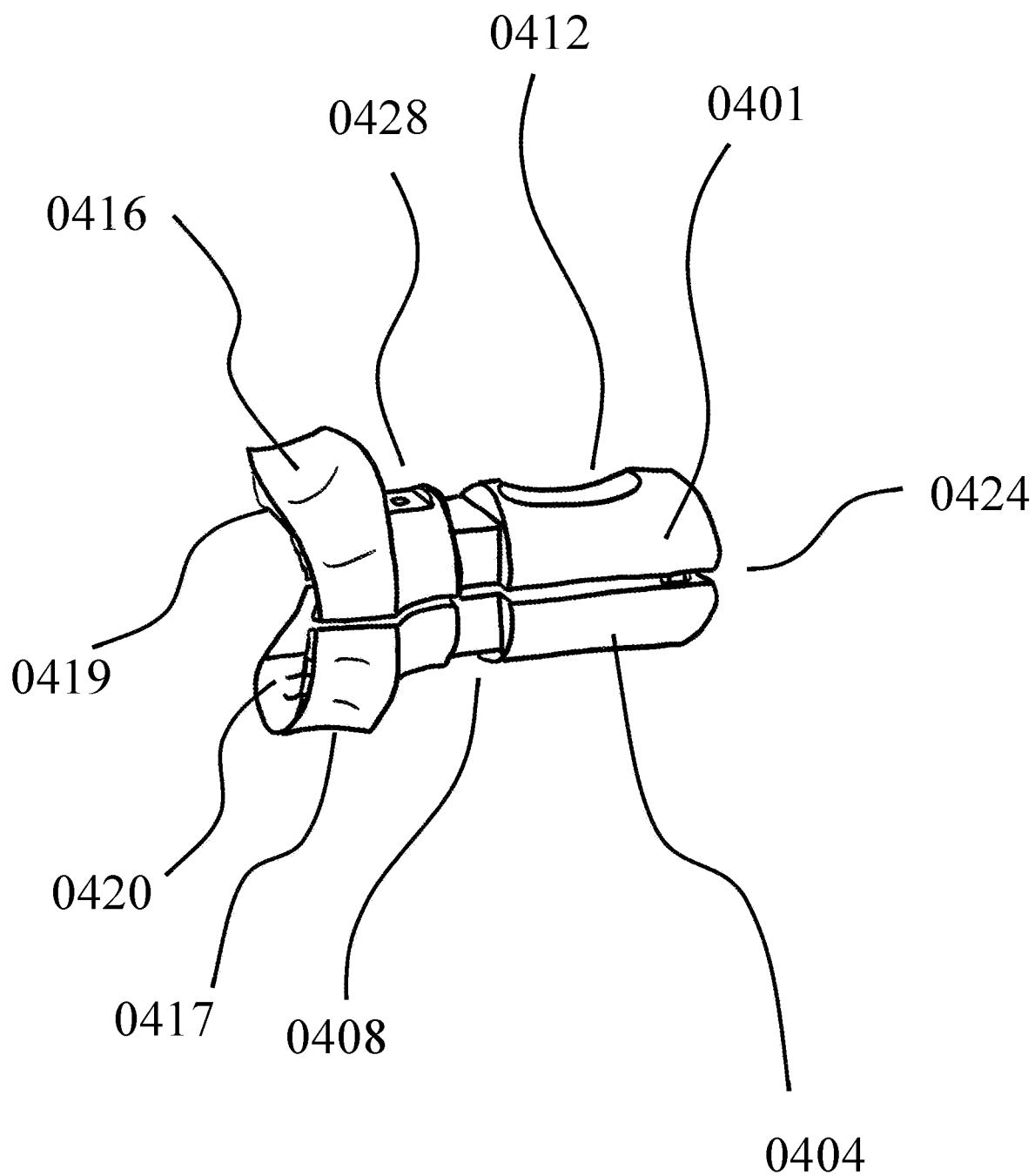
FIG. 4 shows a pair of partially custom-shaped holders to clamp a custom-shaped preparation post of a dental implant intended to receive a dental crown.

FIG. 4 illustrates a pair of partially custom-shaped holders (0401, 0404), including an exemplary hinge design (0424), an upper indent or recess (0412) and a lower indent or recess disposed opposite to the upper indent or recess (not pictured) to indicate the area intended to be held by the fingers of a user. Custom-shaped holders (0401, 0404) further include a slot or a furrow (0408) to be received by a portion of a flat sheet material insert (e.g. 0104, 0304), or by a dedicated guide rail or bearing of the casing, a notch or a mark (0428) to indicate a certain orientation, a pair of custom shaped outer portions (0416, 0417), present in each one of the pair of holders (0401, 0404), respectively, and a pair of custom shaped inner portions (0419, 0420), present in each one of the pair of holders (0401, 0404), respectively. Upper indent or recess (0412) and lower indent or recess disposed opposite to the upper indent or recess (not pictured) are accessible to the fingers of the user when the complete ensemble of implant, holders and inserts is still located inside the package. Slots (0408) are shaped conforming to the dimensions of the inserts (e.g. 0104, 0304). It must be noted that the use of inserts can be avoided if the casing is equipped with mounting means so that the holders can be pushed directly into the casing.

A degree of freedom when inserting the implant into a body cavity is the rotational orientation. Accordingly, it is preferable to mark at least one holder so that the rotational orientation of the implant is clearly indicated. In FIG. 4 holder (0401) bears a notch (0428) specifying the holder placed on the vestibular side of the implant.

Custom shaped outer portions (0416, 0417) are shaped according to the crowns of the teeth being adjacent to the implant. In most cases, the implant will be bordered at least on one side by another tooth (or a crown, bridge, or another implant), and when inserting the implant into the cavity with the help of the holders, the holders must not collide with the adjacent crowns or prosthetic components. Since the available space in the dentition is very limited, it may be required to shape the outer portions of the holders according to the adjacent crowns to avoid interferences.

Custom shaped inner portions (0419, 0420) are conforming to the outer shape of the portion of the implant connecting to the abutment. In an exemplary embodiment, the shape of the implant is designed with the help of a computer. The three-dimensional design data of the implant are then used to define portions (0419, 0420), for instance by using a holder design obtained from a library, providing excess material where the holders are gripping the implant, and using a software like the CAD software application called MAGICS (Materialise, Leuven, Belgium), for example, to remove the excess material by performing a Boolean operation, in this case a subtraction.

When a virtual representation of the custom-shaped preparation post of the implant, intended to receive a crown, is subtracted from the virtual representations of the holders, virtual representations of custom shaped inner portions (0419, 0420) will be generated representing the exact negative of the implant, and thus be perfectly shaped to grip or clamp the implant. The virtual representation of the custom-shaped preparation post of the implant may be positively or negatively sized, or reduced or enlarged by CAD operations, at least partially, to account for manufacturing tolerances or shrinkage in the manufacturing process. The same may apply to the virtual representations of custom shaped inner portions (0419, 0420) of the holders.

In a next step, the so-called "stitching" functionality of MAGICS may be used in case gaps are present in the resulting 3D surface. The outcome of this step is a virtual representation of a solid. In this context, a three-dimensional solid is an unambiguous numerical description of the surface of the geometrical shape of a three-dimensional object, with the numerical description showing no holes and clearly identifying the inside and the outside of the surface.

The data derived from CAD operations in stereolithography (STL) data format is then converted, for example, to an initial graphics exchange specification (IGES), or similar, data format. To fabricate a ceramic holder, for example, a piece of dental zirconia ceramic having a size of approximately 20 mm×8 mm×10 mm using a traditional 5-axis computer numerical control (CNC) milling device with a high-speed spindle (about 60,000 rpm), a spherical tungsten cutter having a diameter of the tip of the cutter of 1 mm and water cooling, can be used. The ceramic workpiece is clamped to the machine table of the milling machine. After programming the machine for the position and inclination of the workpiece, dialing in the machine and process parameters, and overlapping the physical workpiece with the virtual shape, a first portion comprising the generic parts of the holder (the slot receiving the inserts, and the indent or recess intended to be held by the fingers of a user) is completed by grinding down layer-by-layer the workpiece to the shape of interest. Then the completed portion of the workpiece is clamped into a fixture.

After programming the machine for the position and inclination of the reoriented workpiece clamped into that fixture, and entering machine and process parameters and overlapping the physical second part of the workpiece with the virtual shape of the second portion to be machined, the customized portions of the surface are machined by grinding the workpiece down layer-by-layer to the desired shape. After properly cleaning, removing the excess, and degreasing, the workpiece is sintered and finished, the ceramic holder then being ready for use.

Methods of fabricating holders, inserts, and the enclosing container include, but are not limited to, depositing, sintering, 3D printing, molding, curing, grinding, and milling. The ongoing progresses made in rapid prototyping, that is fabricating individual parts directly based on digital data, can strongly contribute to advancing various embodiments of the present invention.

Process steps derived from rapid prototyping can also be used to contribute partially to the manufacturing process. For example, a layer-by-layer wax printing machine fabricates a three-dimensional wax representation (sample) from the three-dimensional design data. The sample is prepared and embedded for lost wax investment casting; the wax sample is burned out and the investment mold is filled with liquid precious metal (e.g., dental gold alloy). After cooling down to room temperature, the embedding material is removed, the runner is cut-off and the workpiece is cleaned.

It must be understood that portions (0419, 0420) need to be customized only in case the corresponding portion of the implant is also customized. If that portion is generic, no customization is required. Different manufacturing technologies may be employed to fabricate the generic-shaped surfaces and to custom-shape the specific surfaces of the holder(s).

FIG. 4 also shows hinge (0424), which serves as a bearing or support to ensure firm clamping of the implant. When being gripped at recess (0412), the gripping force will be distributed in a controlled manner to hinge (0424) and inner portions (0419, 0420), thus providing clamping force to hold a dental implant.

Figure 5:
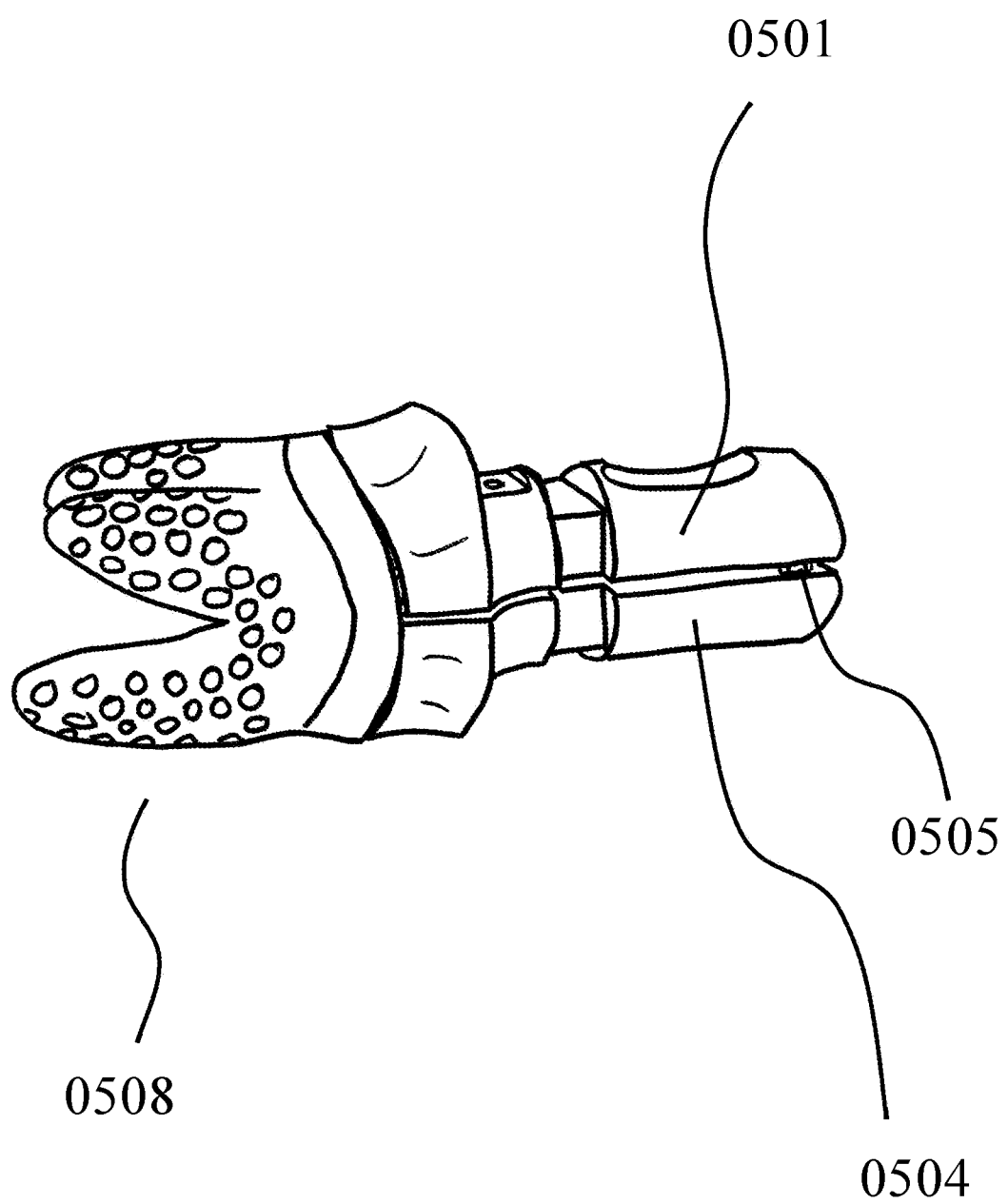
FIG. 5 shows the pair of partially custom-shaped holders of FIG. 4 clamping, according to one embodiment of the present invention, a custom-shaped preparation post of a one-piece, custom-shaped, multi-rooted, root-analogue dental implant.

FIG. 5 illustrates a pair of partially custom-shaped holders (0501, 0504) clamping a custom-shaped preparation post of a single-piece, custom-shaped, multi-rooted, root-analogue dental implant (0508), so that a hinge (0505), analogous to the hinge (0424) shown in the embodiment of FIG. 4, and the fit of the inner custom shaped portions, analogous to (0419, 0420) according to the embodiment shown in FIG. 4, matching the three-dimensional shape of the preparation post of the dental implant (0508), actually clamps the dental implant (0508) when operationally being gripped and held together by the operator, or alternatively a receiving element, as exemplarily shown in the embodiment of the flat sheet insert (e.g. 0104, 0304). The hinge, which is, for example an extension of one holder placed in an indentation of the other holder, may restrict certain degrees of freedom in the relative movement between the two holders, so that the holders having a predefined position towards each other in order to increase the reliability of the clamping or gripping function of the prosthesis, when manually used.

Figure 6:
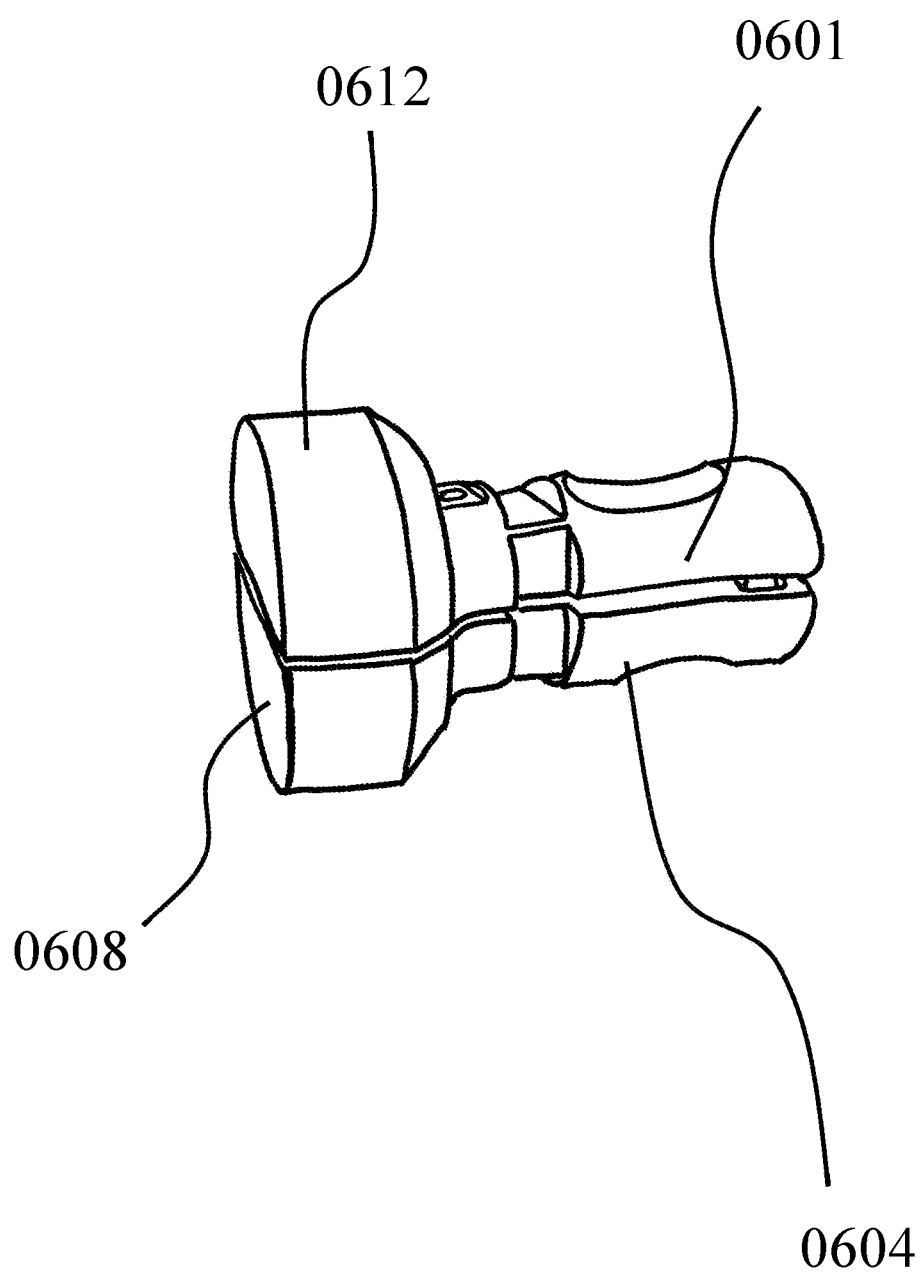
FIG. 6 shows the pair of holders of FIG. 4 prior to the process step of partially custom shaping.

FIG. 6 shows a pair of holders (0601, 0604) where a pair of outer portions (0612), and a pair of inner portions (0608) are pre-fabricated to be further custom shaped. The design of the custom-shaped surfaces is derived as previously disclosed by using a CAD software like MAGICS, which allows material subtraction from the holders (0601, 0604) to customize the inner portions (0608), and to subtract the shape of the adjacent crowns to customize the outer portions (0612). The 3D shape of the adjacent crowns can be obtained using a variety of methods.

For the design of the root-analog implants, sophisticated imaging processes like for example CT (Computerized Topography), CBCT (Cone Beam Computed Tomography), or MRT (Magnetic Resonance Tomography) will be used to acquire the 3D data of the original tooth, and the surrounding tissue. These data will also comprise the crowns of the adjacent teeth, and can readily be used to generate outer portions (0612). Other options include performing a 3D scan of an impression of the dentition, or a 3D scan of a casted model poured from such an impression, or a direct 3D scan of the patient's dentition using an intra-oral 3D camera. Further suitable imaging methods include, but are not limited to ultra sound, destructive scanning, active triangulation, passive triangulation, confocal scanning, and Time of Flight (TOF). Such methods generate either surface descriptions, for example, in STL-format, or volumetric data, for example, in a so called "voxel"-format that can be transformed into surface data by generally available software applications known to those skilled in the art, and vice versa.

The digital surface data consists of multiple measurement data points, each having an x, y, and z coordinate and together having a density better than 0.1 mm and an accuracy noise of less than 0.05 mm. Alternatively, other resolutions, accuracies, and coordinate systems including, but not limited to cylindrical or spherical coordinate systems, can be employed by those skilled in the art. The data points are then exported in STL format according to this exemplary embodiment of the present invention. This widely used file format describes a surface or portions of a surface by interconnected triangles. STL files can be encoded either in binary or in ASCII format. Other established formats like PLY are also applicable.

Figure 7:
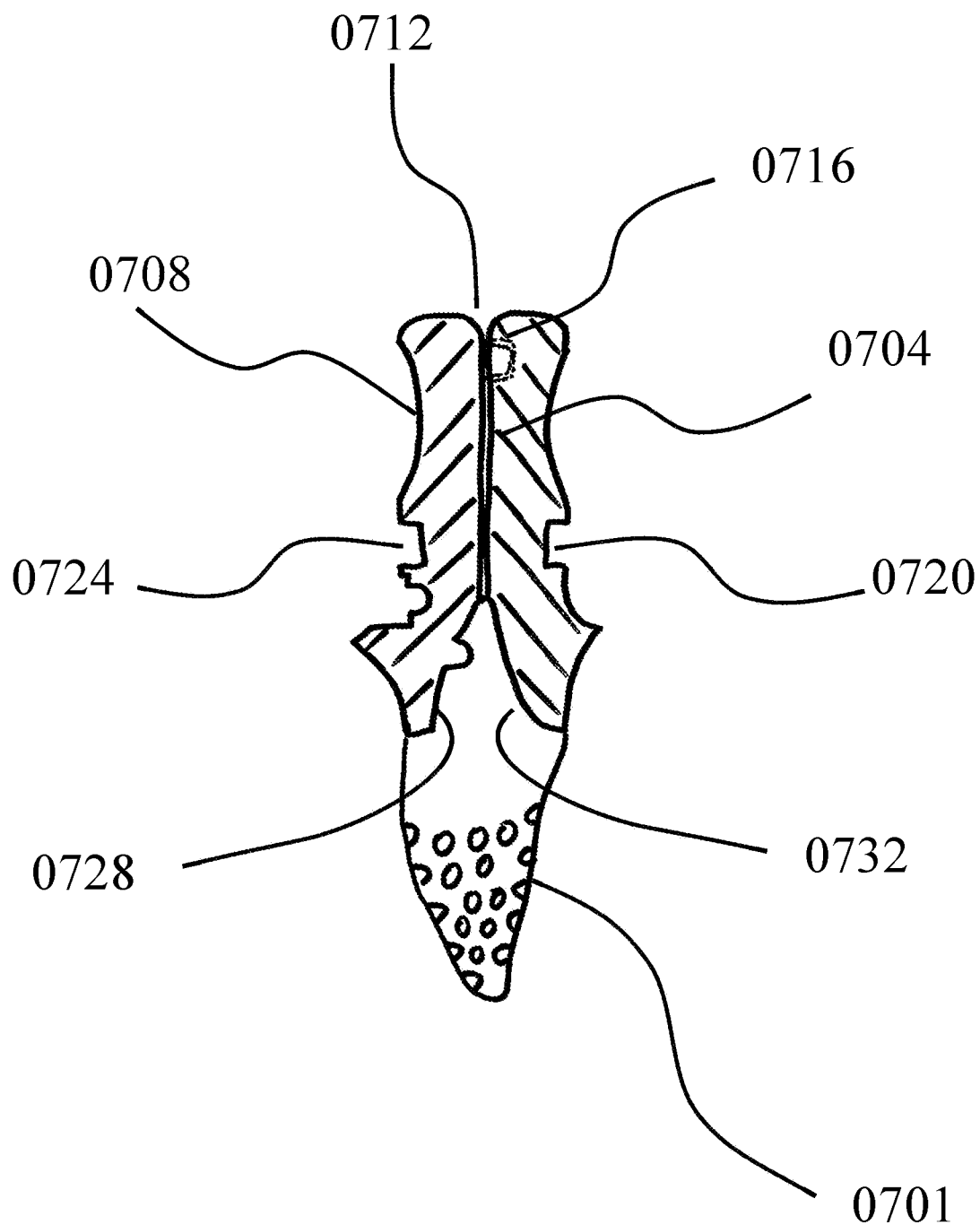
FIG. 7 shows a partial cross-sectional view of a pair of holders clamping a custom-shaped preparation post of a one-piece, single-rooted root analogue dental implant.
Figure 8:
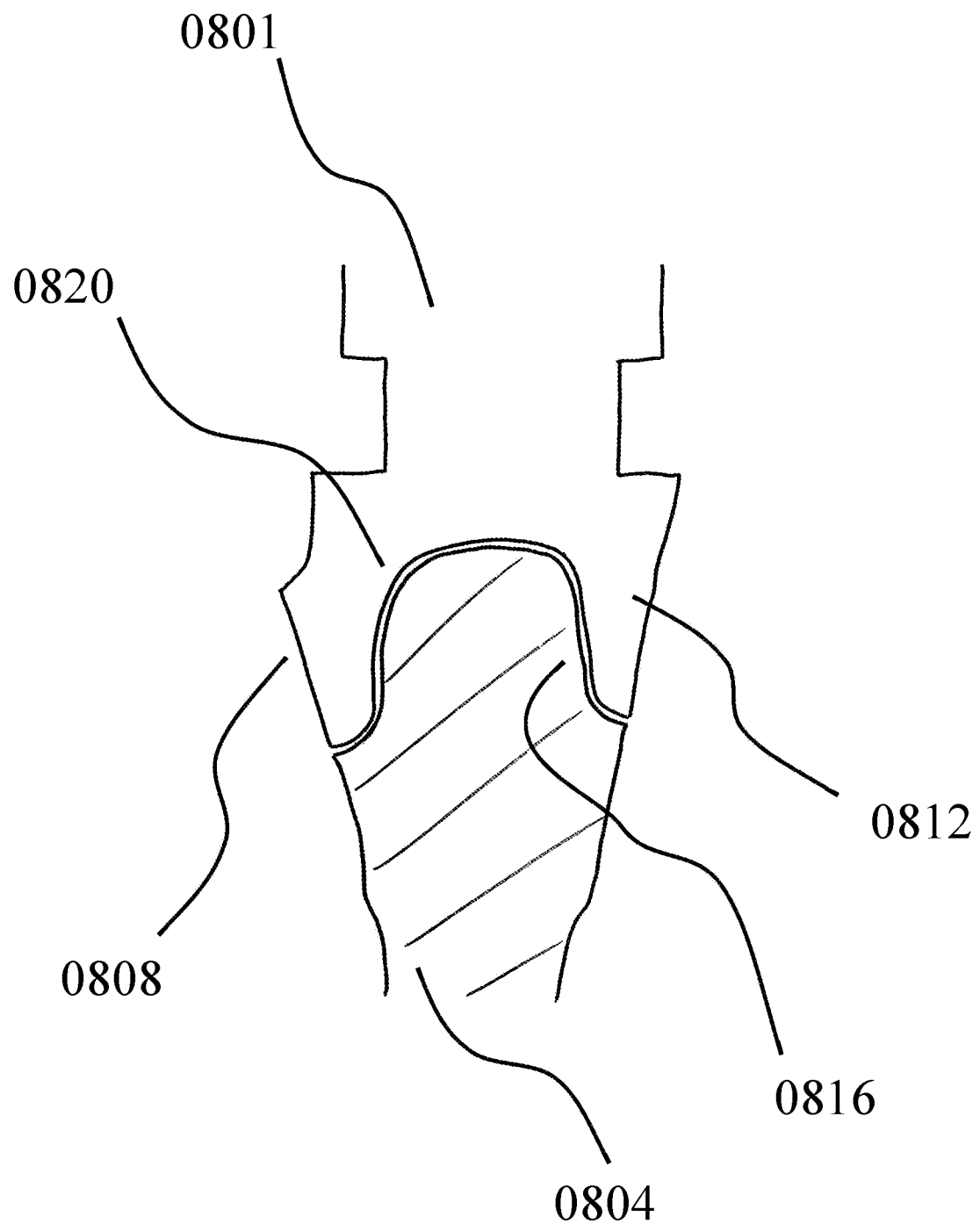
FIG. 8 shows a partial cross-sectional view of one of the pair of holders clamping the custom-shaped preparation post of the one-piece, single-rooted root analogue dental implant of FIG. 7.
Figure 9:
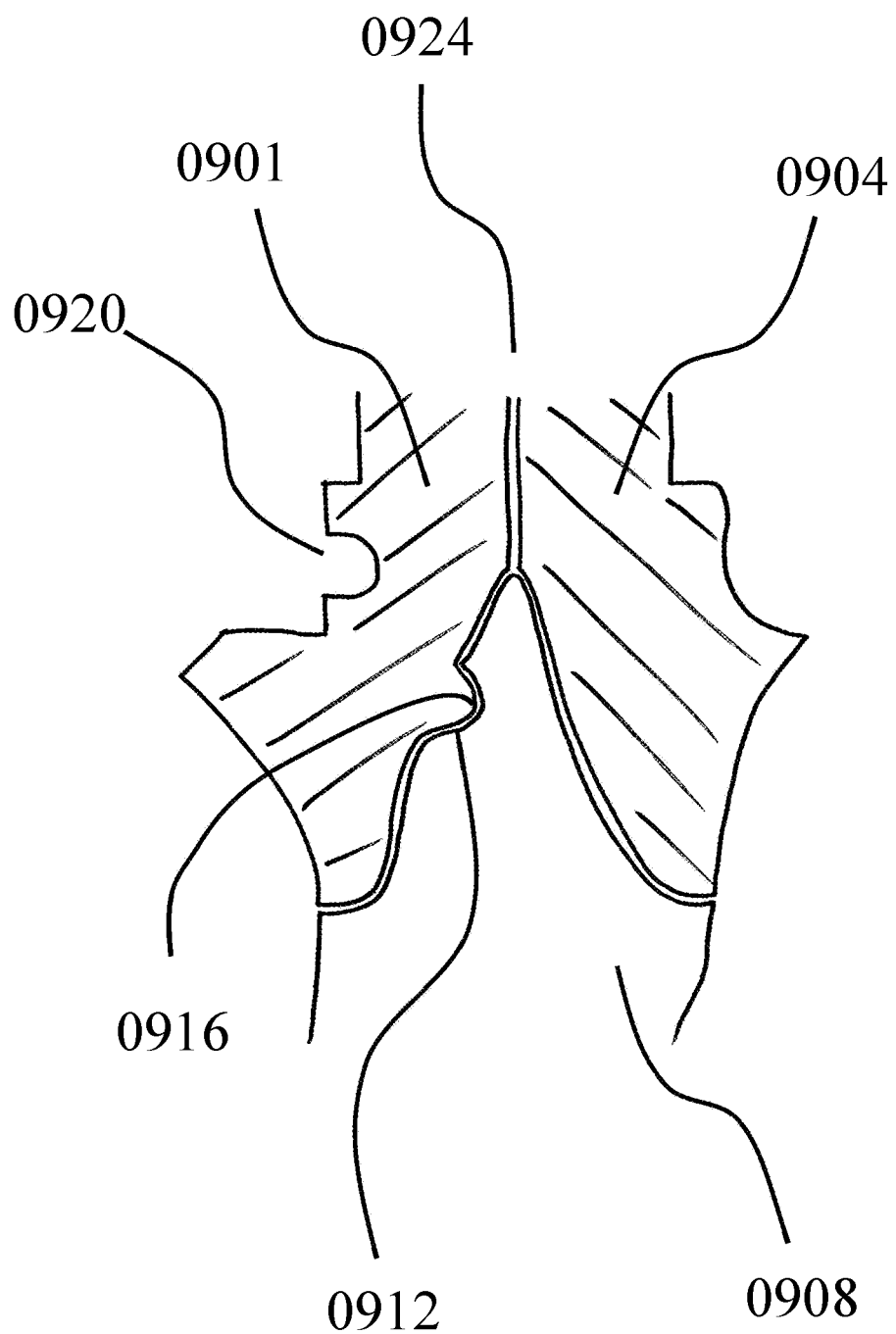
FIG. 9 shows a partial cross-sectional view of one of the pair of holders clamping the custom-shaped preparation post of the one-piece, single-rooted root analogue dental implant of FIG. 7 in a view perpendicular to the view of FIG. 8.

FIGS. 7, 8, and 9 illustrate exemplary holders (0704, 0708, 0801, 0901, 0904) clamping exemplary custom-shaped preparation posts (surfaces 0728, 0732, 0816, 0912) of one-piece, single-rooted, root-analogue dental implants (0701, 0804, 0908). In an exemplary embodiment, the surfaces of the implants' preparation posts and the corresponding custom shaped inner portions of the holders are showing additional slot and key features (e.g. 0916) providing undercuts. These undercuts provide an additional interlock, securing the implant safely to the holders even if the ensemble is held with moderate force. For example, the custom-shaped preparation post of the dental implant is intended to receive a dental crown, and a custom-shaped portion of at least one of the holders includes an inverse or negative shape of a preparation post matching a corresponding surface of the preparation post of the dental implant.

FIG. 7 also explains the mechanism of hinge (0716). The noticeable gap (0712, also shown as 0924 in FIG. 9) between holders (0704) and (0708) prevents contact between the holders (0704) and (0708), and they do not absorb any forces. Rather, when the holders are gripped at the recess, the gripping force will be supported only by hinge (0716), and by surfaces (0728) and (0732), which ensures a stable and reliable seating of the implant within the holders.

In addition, FIG. 7 shows two slots or furrows (0720) and (0724). These slots serve as receptacles for inserts (0304 in FIGS. 3, and 1004 in FIG. 10), or can slide directly into guide rails (not pictured) of the casing. Guide rails of the casing could be designed to show a certain degree of elasticity, thus fixing the holders by frictional forces, or a movement of the holders in the rails could be prohibited by the closure of the casing, or a combination thereof. In addition, the guide rails can be designed so that they can be intentionally deformed by the user in order to release the frictional forces, thus allowing for easy removal of the holders and the prosthesis from the container.

FIG. 9 also illustrates an embodiment of a mark or notch (0920) allowing the user to handle and insert the prosthesis correctly. In one exemplary embodiment the vestibular side of the dental implant is marked.

Figure 10:
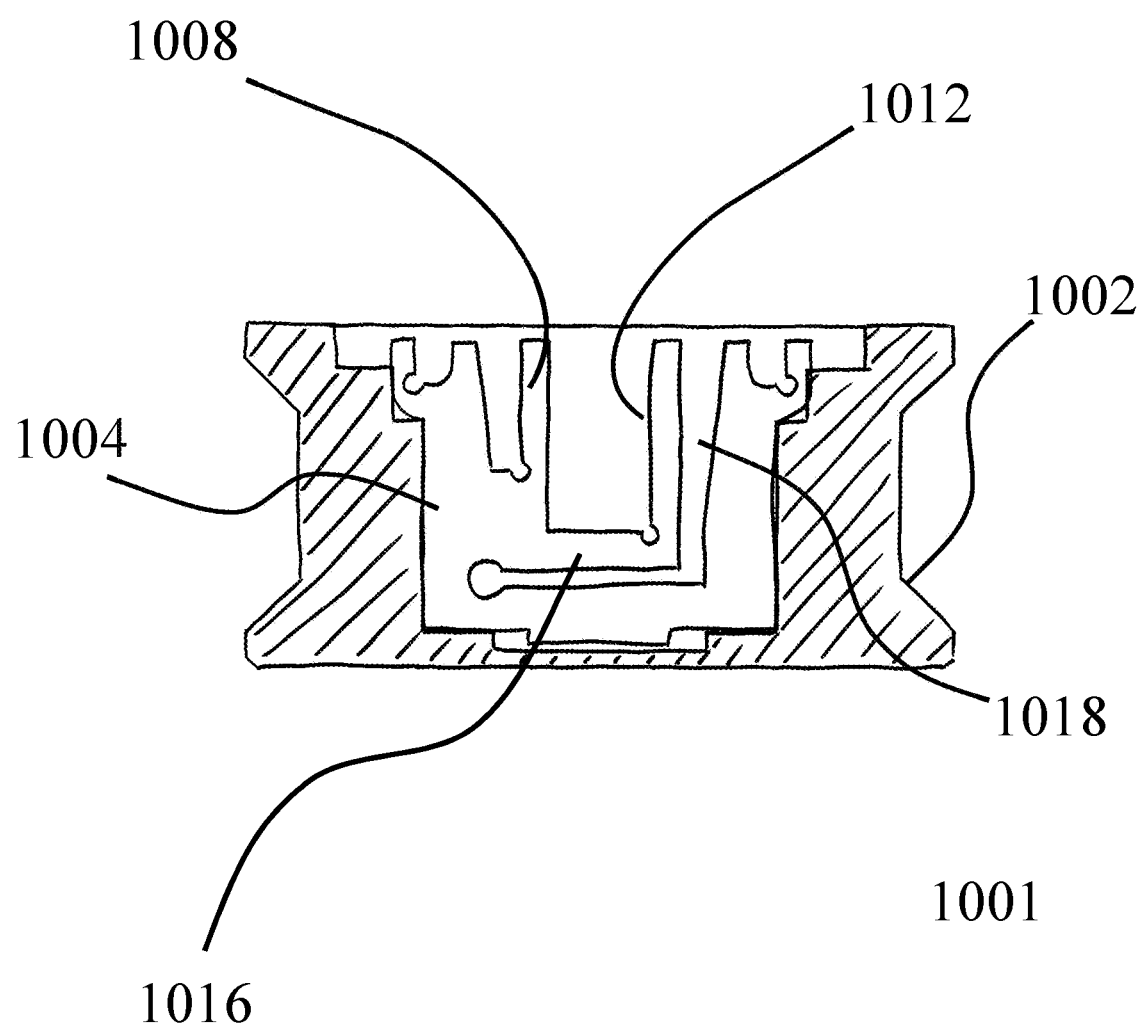
FIG. 10 shows the packaging container of FIG. 1, FIG. 2, and FIG. 3, and details of the flat-sheet material insert for holding the pair of custom-shaped holders, exemplarily shown in FIG. 1, FIG. 2, FIG. 3, FIG. 4, FIG. 5, and FIG. 7.

FIG. 10 shows a packaging container (1001) including a casing (1002), and a flat-sheet material insert (1004) with a cut out, including corresponding surfaces (1008, 1012) to receive and hold in a closed position a pair of custom-shaped or generic-shaped holders. The insert of FIG. 10 comprises several grooves or cut-outs, generating a desired degree of flexibility or allowing for a certain degree of deformation. The holders are located between surfaces (1008) and (1012).

Both edges show a certain amount of flexibility, resulting in an elastic grip of the ensemble of holders and implant. The long cut-out (1018) adjacent the leg (1016) located between the receptacles for the holders provides additional elasticity. The insert (1004) is shaped so that it fit into slots in the casing (1002). These slots can be seen in FIG. 15 (1502). The insert (1004) can slide freely inside the slots (1502). The outer top edges of the insert, however, are manufactured to produce a press fit, so that the insert, once inserted into the casing, will be secured in place. In order to remove the implant from the container prior to implantation, the outer upper corners of the insert are bent slightly inwards with the help of a pair of pliers. This releases the grip force, and allows for forceless removal of the insert and the implant by gripping the implant at recesses (0412 in FIG. 4), and pulling slightly.

The insert as exemplarily shown in FIG. 10 can be manufactured from sheet metal for example by laser or die cutting, water jet cutting, wire erosion, or other applicable processes. In another embodiment, the insert is shaped in order to provide a large surface, and can serve as an additional getter surface. In certain embodiments, there can be one insert or more than one insert for a casing and container, and the one or more inserts can be made from a single, monolithic piece of material, such as sheet metal, or can be made from multiple, connected pieces of material, such as welded metal.

It should be noted that the implementation of the inserts as displayed in FIG. 10 and other figures is an exemplary embodiment. Somebody skilled in the art will be able to design a great variety of inserts, also from different materials, that would equally perform the required function.

Figure 11:
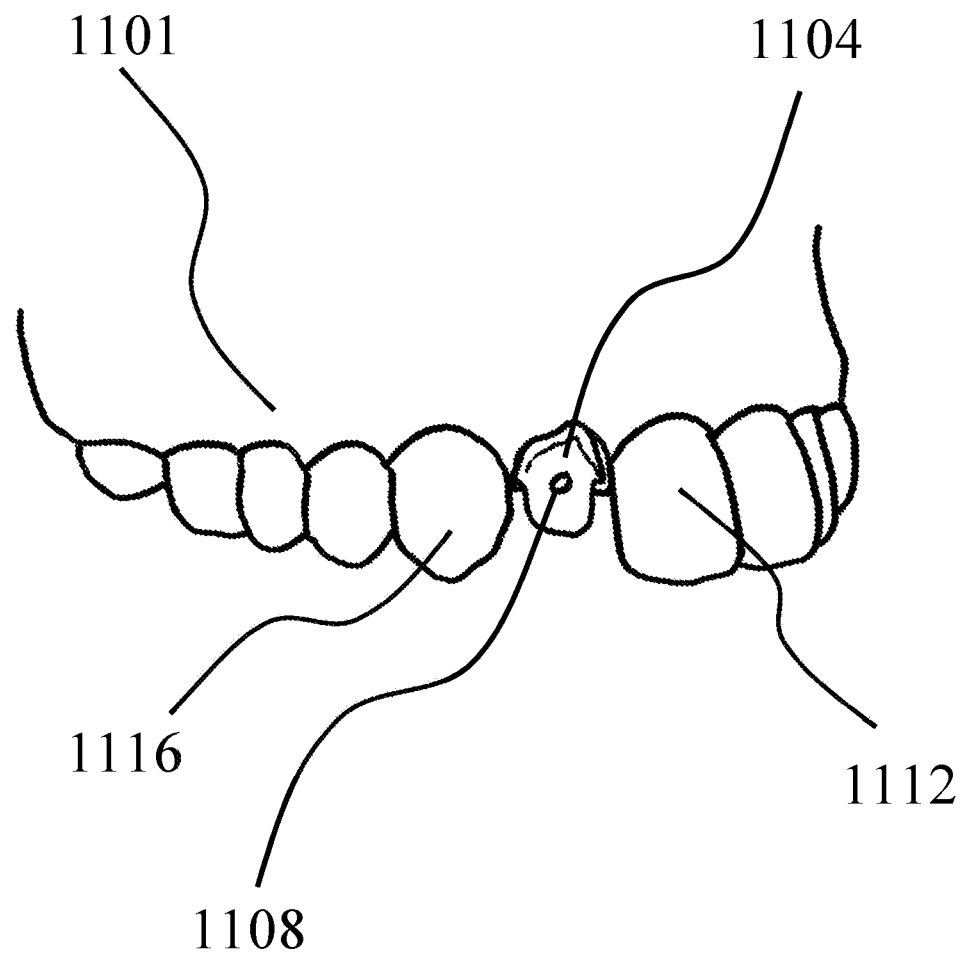
FIG. 11 shows a custom-shaped preparation post of a dental implant, having a vestibular mark, inserted in a suited position and orientation of a human dental anatomy between two adjacent crowns.

FIG. 11 shows a custom-shaped preparation post of a dental implant (1104), having a vestibular notch or mark (1108), inserted in a position of a human dentition (1101) between two adjacent crowns (1112, 1116).

Figure 12:
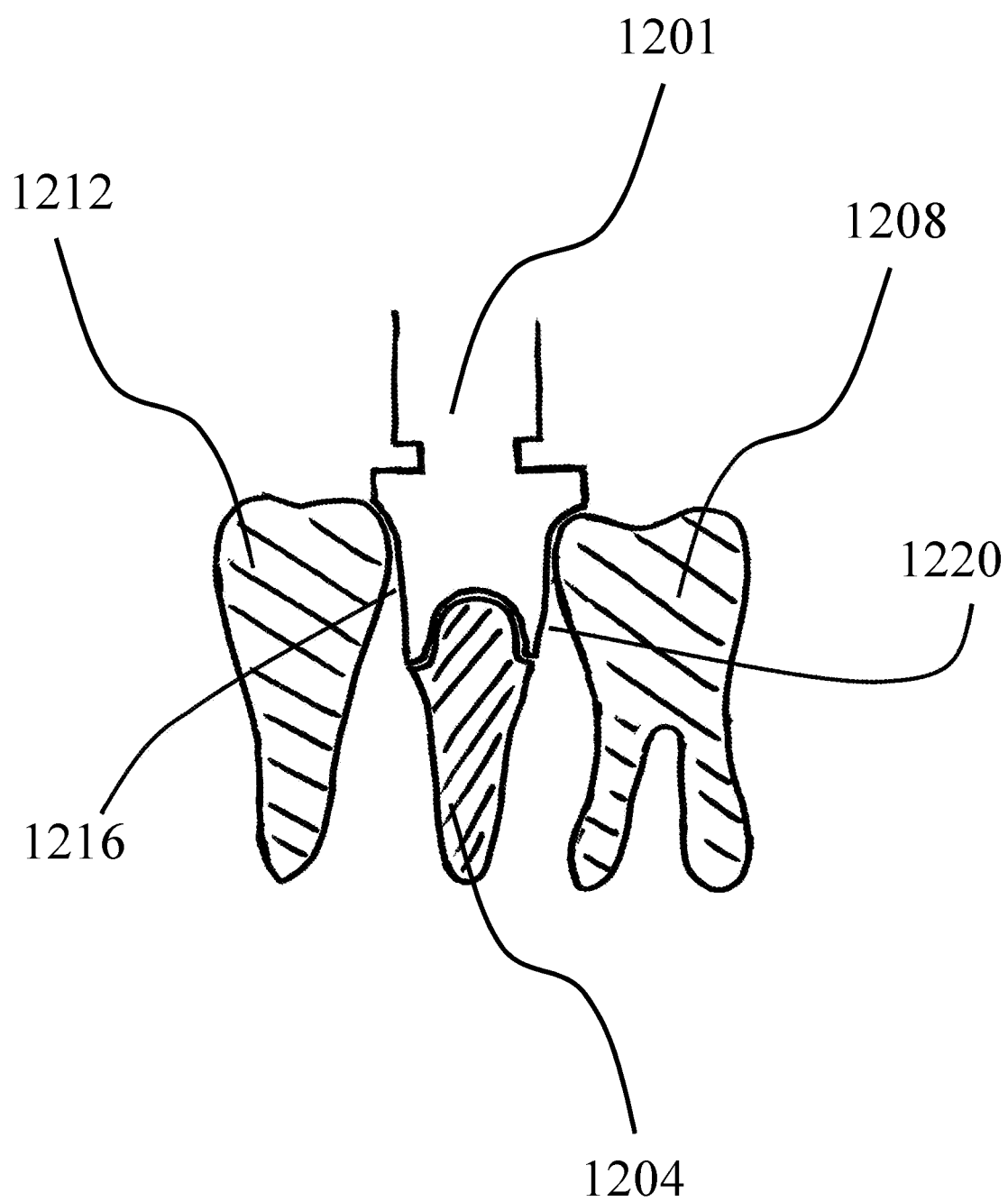
FIG. 12 shows a partial cross-sectional view of a root-form dental implant having a custom shaped preparation-post being held or clamped with a pair of partially custom-shaped holders during the insertion between two adjacent natural teeth.

FIG. 12 shows a root-form dental implant (1204) having a custom shaped preparation-post being held or clamped with a pair of partially custom-shaped holders (1201) during the insertion between two adjacent crowns (1208, 1212). The outer portions (1216) and (1220) of the holders are customized to conform to the corresponding surfaces of the adjacent crowns, providing a defined degree of freedom. As disclosed with respect to FIG. 6, the virtual shape(s) of the outer portions (1216) and (1220) can, for example, be derived by obtaining 3D data of the adjacent crowns, and by performing a Boolean operation (in this case a subtraction) in order to remove at least all portions from the virtual representation of the holders that would otherwise, when accordingly fabricated, interfere between the holders and the adjacent crowns.

The CAD software MAGICS also has functions allowing an orthogonal shift of the surface of an object by a specified amount. This allows reduction of a 3D body, and thus to create a small gap between the outer surface of the holder, and the outer surface of the crown, allowing for a certain degree of maneuverability. MAGICS has helpful features that have originally been developed to optimize plastic parts for injection molding, but also have been found to be useful for the processes of various embodiments of the present invention.

The STL data describing the surfaces or solid representing the holder are then, for example, converted to an IGES data format. This is performed using, for example, software named SolidWorks (SolidWorks Corp., Concord, Mass. USA). The IGES file allows generating a CNC sequence to machine an artificial tooth from a piece of material like titanium or a titanium alloy (like Ti6Al4V), that consists, for example, of more than 60% of titanium. Ceramic material and other biocompatible materials or materials suitable for packaging medical devices, including but not limited to stainless steel (like 1.4435, 1.4542 or 1.4548), synthetics, elastics, plastics, resin-modified glass-ionomer cement, hybrid-ionomer cement, resin-enforced cement, and other synthetic and plastic materials, are also applicable. Processes to manufacture solid parts based on digital 3D data are also described in the aforementioned '537 application.

In another embodiment the holders are made from metal, and so-called rapid prototyping processes like selective laser melting are used to manufacture the holders. A wide variety of materials and manufacturing processes are applicable to produce holders showing the required properties. The main requirements regarding holders and inserts are that they must withstand the processes used to ensure the purity of the implant, which may include sterilization and/or plasma cleaning. In an exemplary embodiment, both the insert(s) and the holder(s) must maintain their shape during those processes.

In another embodiment of the present invention, the holders are made from stabilized tetragonal zirconium oxide polycrystalline or another aluminum oxide or zirconium oxide material known to those skilled in the art (e.g. inCoris ZI, inCoris AL, VITABLOCS, and CEREC Blocs distributed by and Ivoclar Vivadent and SIRONA). Alternatively, the holders can be made of titanium or a titanium alloy and surface coated with zirconium oxide, for example, in sputtering technologies (as offered by Clinical House Europe GmbH). In yet another embodiment, the packaging components are at least partially made of one of the following, or any combination of the following: titanium, titanium alloy that consists of more than about 60% of titanium, cement, zirconium oxide, ceramics, synthetics, elastics, plastics, stainless steel, glasiomer cement, resin-ionomer cement, hybrid-ionomer cement, resin-enforced cement, and acrylic based photopolymer.

In yet another embodiment of the present invention, a rapid prototyping process is used for fabricating the holders and/or the packaging container and/or the inserts from hybrid materials. The rapid prototyping process may build the holder layer-by-layer. For example, a powdery layer of a substance can be applied on top of a workpiece, and then portions of the new layer are hardened by a controlled laser beam, while the other unhardened portions are later removed. In this manner, different substances having different properties (stiffness, hardness, biological properties etc.) can be applied, and therefore different portions of the workpiece are made from different materials. In an embodiment of the present invention, the portion of the holders enclosing the prosthesis is made from a material different from the one used for the generic portion with slot and recess.

In yet another embodiment of the present invention, the holders, inserts or the container are an assembly of two or more parts. The parts are, for example, glued, sintered, mounted by pressure, and/or screwed to each other. In yet another embodiment of the present invention, the segments are fabricated using different materials and manufacturing technologies.

Figure 13:
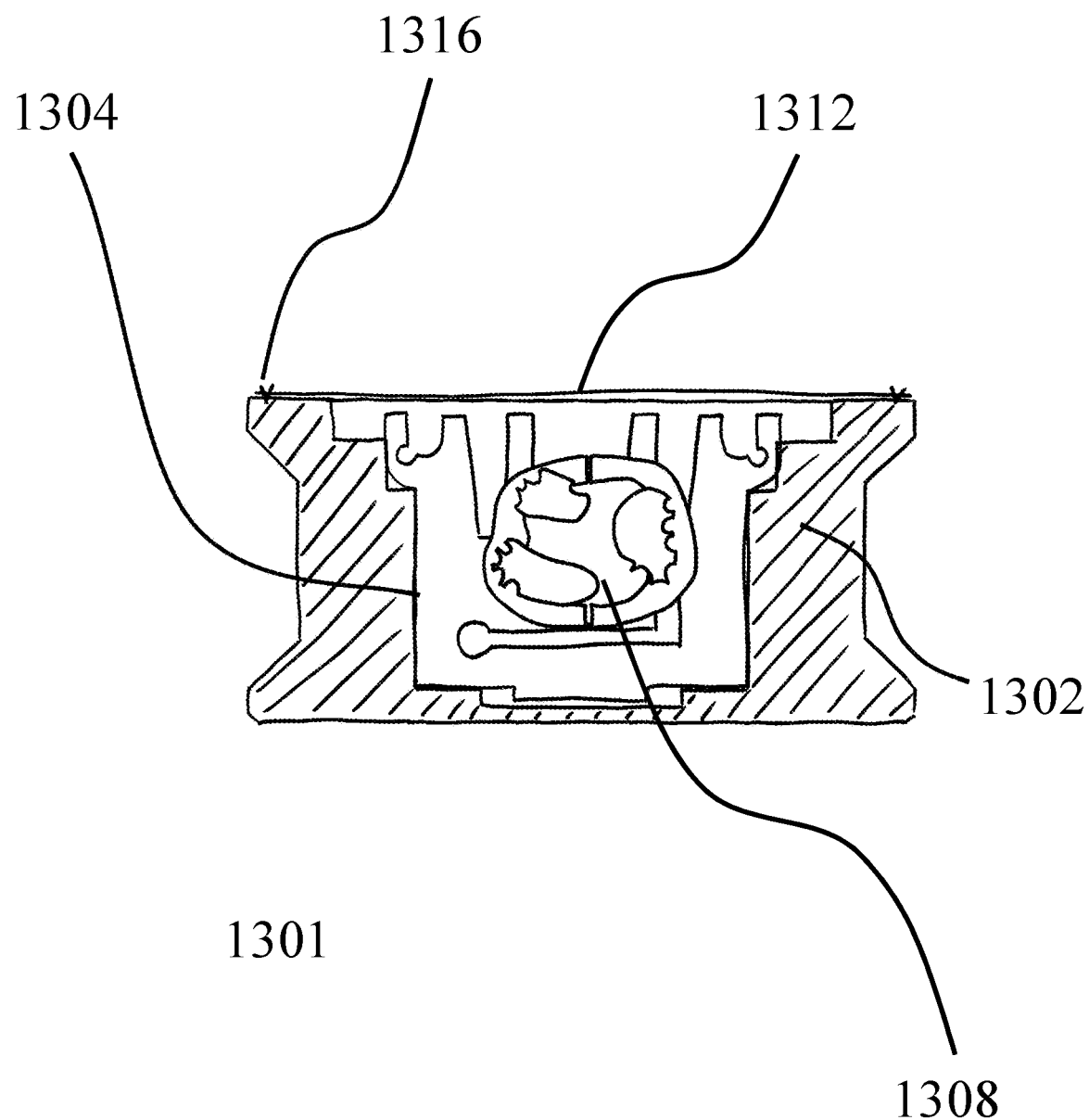
FIG. 13 shows a partial cross-sectional side view of a hermetically sealed packaging container having the custom-shaped, multi-rooted, root-analogue dental implant disposed within the container as shown in the embodiments of FIG. 2 and FIG. 3.

FIG. 13 shows a cross-sectional view of a packaging container (1301) including a casing (1302) being hermetically sealed with a foil (1312), for example with a thickness of about 10 to about 1000 micrometers, e.g. about 50 micrometers, that is circumferentially welded (the welding seam indicated as 1316, also shown as 1420 in FIG. 14), having fixated a custom-shaped, multi-rooted, root-analogue dental implant (1308) in an insert (1304) made from flat sheet material. In order to preserve the surface properties of the implant to the maximal extent, an air-tight closure of the packaging container is required in some embodiments. Considering the cost and required effort of an implantation procedure, and the grave consequences of a failure of hard and soft tissue integration, the functionality of the package has utmost priority, compared to cost savings.

Accordingly, an exemplary embodiment comprises a disposable container. The outer shell of the container is made from only two pieces: the frame-like casing (1302) comprising the walls of the container and the bottom portion, and foil (1312) forming the seal of the container. A great variety of materials and processes is available for manufacturing and processing the foil. In an exemplary embodiment, the foil is laser-welded to the container. A circumferential weld seam ensures hermetical closure. In an exemplary embodiment the laser source is a fiber laser, emitting light at a wavelength of about 1070 nm. The laser beam is focused by optic components to a spot size of about 50 micrometers. The travel path of the laser light spot is numerically controlled by a two-axis or three-axis mirror system. Also, other laser technologies are readily available.

Another option is a design where the bottom closure is not a part of the frame, but consists of another foil, which is welded to the frame using the same mechanism as for the upper closure. Yet another example would be to use a container fabricated by deep-drawing instead of milling. Further variants like selective laser melting have been mentioned with respect to FIG. 1. Instead of welding a foil to the frame-like casing (1302), another option is to use this portion as a mechanical fixture for the prosthesis only, and to enclose this fixture by one or more foils that would be welded to each other. The packaging container could also be made from a tubular material, having for example a circular or rectangular cross section, and both openings on the ends of the pipe would be closed by foils.

In yet another embodiment, a foil made from synthetic material is used, having a thin metallic coating, and the container is sealed by heating and welding the plastic material. The examples listed above are reflecting only a fraction of processes and materials suitable for producing the packaging container. Accordingly, other methods of providing an air-tight enclosure can be selected. Welding, border crimping, and soldering, if executed properly, will produce excellent results, but other methods like bonding, vacuum sealing, or using a detachable connection can also serve for creating an airtight enclosure.

Foils having an appropriate thickness can also be connected by hemming and/or creasing. Such a seam may not be as tight as a welded seam, but since the great majority of prostheses are fully customized for treatment of a specific patient, the product will be delivered in a short time frame, and will not reside inside the package for more than a couple of days. In order to control the tightness of the seal, the packaging container can for instance be filled with helium. Helium molecules escaping from the container can easily be detected using a common leakage helium sniffer. Other gases and detection mechanisms are also applicable.

Several designs are applicable to support a reusable or partially reusable container. If the packaging container is for instance formed from a stable frame being enclosed by sealed foils, only the foils are dispensable, whereas the frame would be reused. This concept is also suitable for a tubular container as mentioned above. If a foil is welded directly to a solid frame-like structure, this structure can also be reused a couple of times by milling or grinding off the top layer, thus removing the residuals of the welding seam. If the container is initially fabricated with excess height, this refitting can be performed multiple times.

Figure 14:
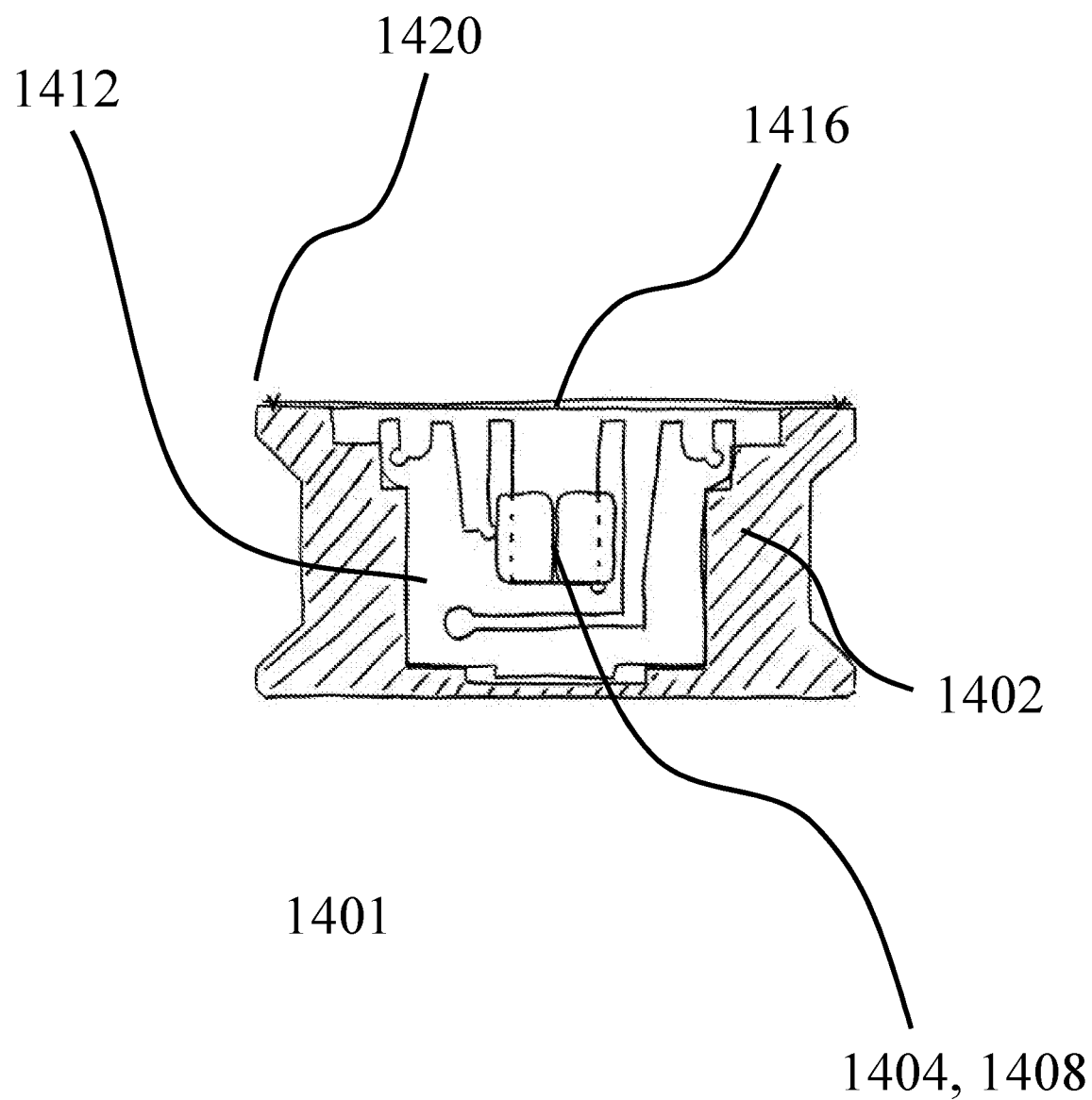
FIG. 14 shows a partial cross-sectional side view from a hermetically sealed packaging container having the pair of holders in a receiving portion of the flat sheet material insert for fixating the custom-shaped, multi-rooted, root-analogue dental implant to be disposed within the packaging container, as shown in the embodiments of FIG. 2 and FIG. 3 in a view opposite to the view shown in FIG. 13.

FIG. 14 shows a cross-sectional view of a packaging container (1401) including a casing (1402) having a pair of holders (1404, 1408) in the receiving portion of the flat sheet material insert (1412) fixating the custom-shaped, multi-rooted, root-analogue dental implant.

FIG. 15 is a top view of a packaging container having fixated a custom-shaped, multi-rooted, root-analogue dental implant and having an additional meandering-shaped flat sheet material (1501) that serves as an additional getter surface. As mentioned previously, it is advantageous to include within the packaging container portions of materials with large surface areas exhibiting the ability to attract and/or retain and/or react with residual impurities, optionally with the ability to act as a catalyst to allow for removal of impurities by chemical reaction on an adsorbing surface of the getter.

Figure 16:
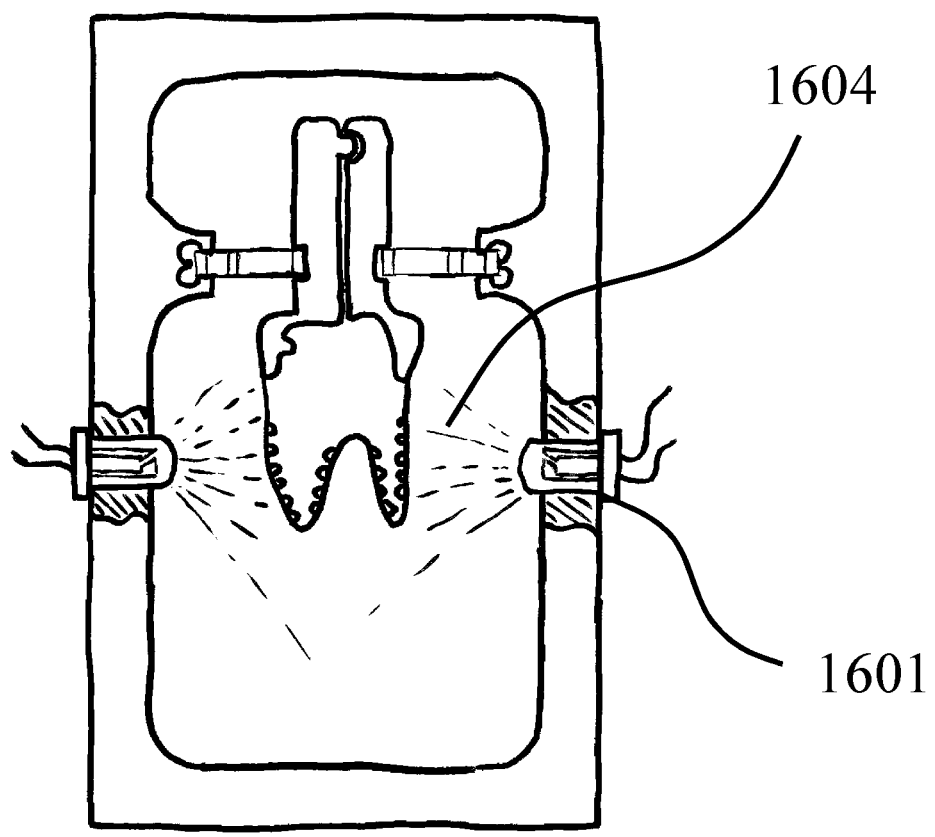
FIG. 16 shows a top view of the packaging container having a custom-shaped, multi-rooted, root-analogue dental implant disposed within the packaging container, having two additional LEDs radiating ultraviolet C (UVC) light.

FIG. 16 shows a packaging container having fixated a custom-shaped, multi-rooted, root-analogue dental implant, and having one or more, in an exemplary embodiment two, LEDs (1601) radiating UVA, UVB, and/or UVC light (1604), for example in the range of a wavelength of about 230 to about 400 nm, e.g. about 250 nm. The LEDs can be permanently connected to a source of electricity, which would require attaching small batteries to the package, or they can be connected to a power source prior to the implantation process, for example by means of at least one isolating lead through into the encasement. In another exemplary embodiment, the energy is transmitted by an inductive process into the encasement. The ultraviolet light is of advantage for disinfection processes, catalytic processes and/or for photo activation, which is a local charge shifting effect, for example, to enhance surfaces of the prosthesis for hard- and/or soft-tissue integration.

Another option to expose the packed implant to UV radiation for removal of impurities is to manufacture portions of the packaging container from quartz glass, allowing for the passage of UV rays to the dental implant through the packaging container (not illustrated in the drawings). In the practice of the dentist or surgeon, the packaging container would be placed into a small cradle comprising UV radiating elements, the elements being configured to match the quartz glass portions of the container.

FIG. 17 lists process steps that may be executed, sequentially or otherwise, in an exemplary embodiment, including surface conditioning of a prosthesis (step 17A), placing a prosthesis clamped in holder components in a packaging container (step 17B, step 17C), sealing the packaging container (step 17D), sterilizing (step 17E) and heat activating (step 17F) and/or UV activating (step 17G) of the prosthesis surfaces, opening the container for sterile delivery (step 17H), and using the holder to place the prosthesis clinically (step 17I).

FIG. 18 lists process steps that may be executed, sequentially or otherwise, in another exemplary embodiment, including: customizing a prosthesis (step 18A), applying a surface conditioning (step 18B), customizing holder components (step 18C), clamping the prosthesis with the holder components (step 18D), inserting the holder with the prosthesis in a metal container (step 18E), sealing the metal container with a metal foil hermetically by laser welding (step 18F), sterilizing the prosthesis inside the sealed container with dry heat (step 18G), or alternatively sterilizing the prosthesis inside the sealed container with beta, gamma or e-beam radiation, opening the container for sterile delivery of the prosthesis (step 18H) and using holder to place the prosthesis clinically (step 18I).

Using computer networks, all process steps may be carried out by different and independent parties. The 3D acquisition of the shape of adjacent crowns, for example, be performed at the dentist's office, at a hospital or at a location specialized in imaging. The imaging data can then be transferred to a location where the imaging data are further processed in order to ready them for manufacturing. Then, the data can be transferred to a remote manufacturing location. All of these data transfers can, for example, be performed via the Internet, using preferably Virtual Private Network channels to secure privacy, or through a local area network.

Figure 19:
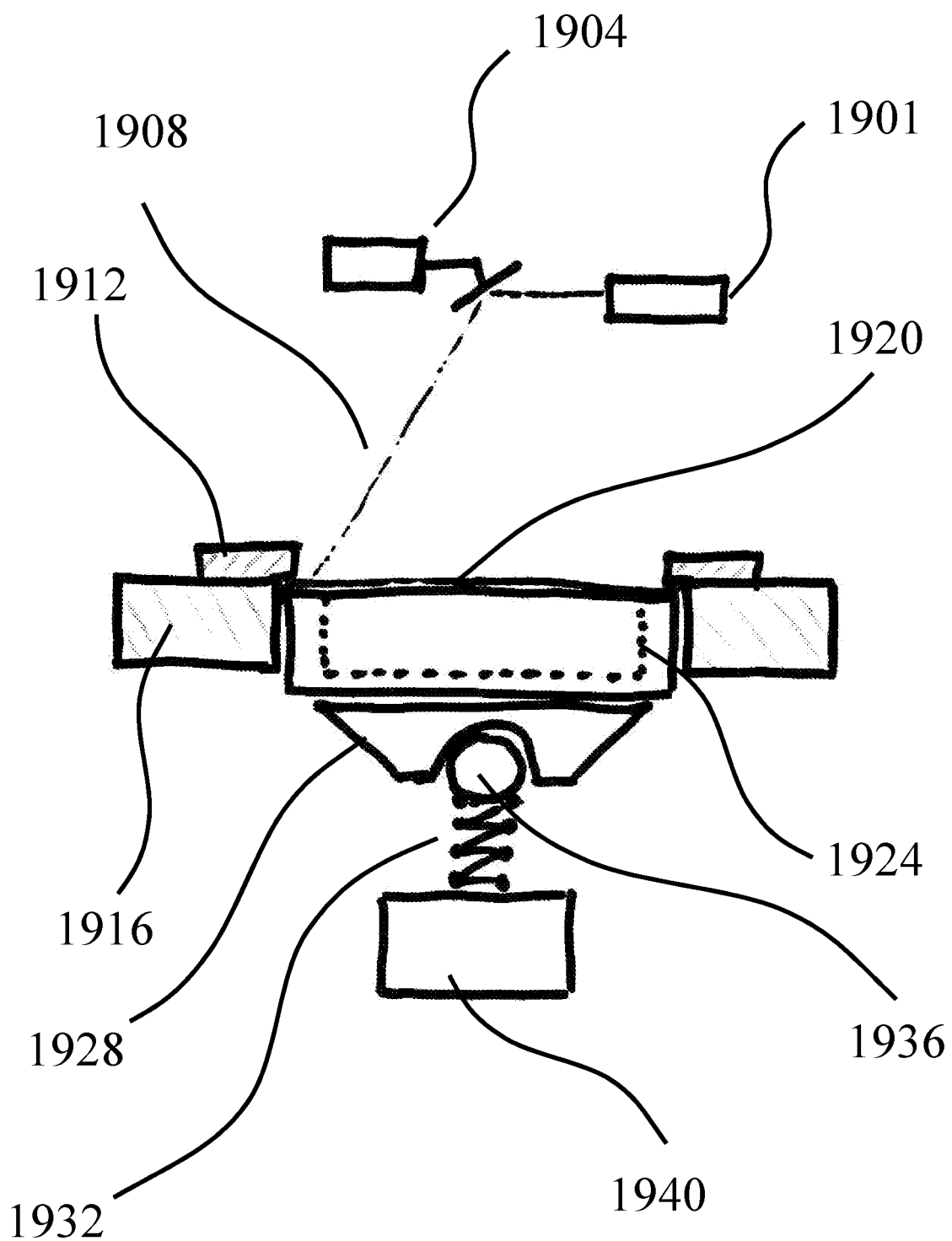
FIG. 19 shows a system for laser welding including a tool to hold a casing and a foil in very close proximity of each other, compensating for dimensional variances in height of the casing.

FIG. 19 provides a brief overview of a system for laser welding, including a laser source (1901), an actuator-controlled two-axis or three-axis mirror system (1904) directing the beam (1908), a tool base (1916) to hold a container (1924), and a foil (1920) in very close proximity to container (1924). The fixture of container (1924) is spring loaded to avoid gaps between container (1924) and foil (1920). The fixture comprises a base (1940), a spring (1932), a swivel (1936), and a support (1928). This design allows the container to adjust in two rotational degrees of freedom, and distributes the forces induced by the spring to fixate and hold close against frame (1912) and tool base (1916), independent of thickness variances of container and/or foil.

Such variances can result from the raw material used for the container, from manufacturing processes, and divergences in thickness of the foil. Base (1940), tool base (1916) and frame (1912) must be interconnected in order to function properly. This connection is not illustrated in the drawing. The spring (1932) is configured to apply, for example, a force in the range of about 1 to about 500 N, e.g. about 50 N to press the foil against the container. The allowable gap between the container surface and the foil for laser welding is, for example, in the range from direct contact to up to about 100 micrometers, so that the requirement for the evenness of the container, for example needs to be better than about 100 micrometers, e.g. up to about 10 micrometers. The mechanism(s) to open and load the fixture and to apply the spring forces are generally known to one skilled in the art.

A system including one or more mirrors to direct the laser beam ("remote laser cutting") has several advantages over a system with a fixed beam where the container would be moved. In an exemplary embodiment, the shape of the welding seam is specified by numerical data being fed into the system ("numerical control"). From the numerical data defining the welding path, the system calculates the required movements of the mirror(s). In this manner, curved seams can easily be achieved, just as well as a seam composed only from straight portions. Other systems may comprise a flexible fiber to transmit the laser energy to the welding spot. Additionally, after the welding process, the laser can be used to trim or cut off foil excess adjacent to the welding stream.

In an exemplary embodiment, the laser configuration of FIG. 19 is used to add labelling and/or tagging by marking and/or inscription onto the encasement surfaces. In this context, for example, different laser energies or intensities are used to change surface color, for example, on materials that include titanium.

Figures 20A, 20B:
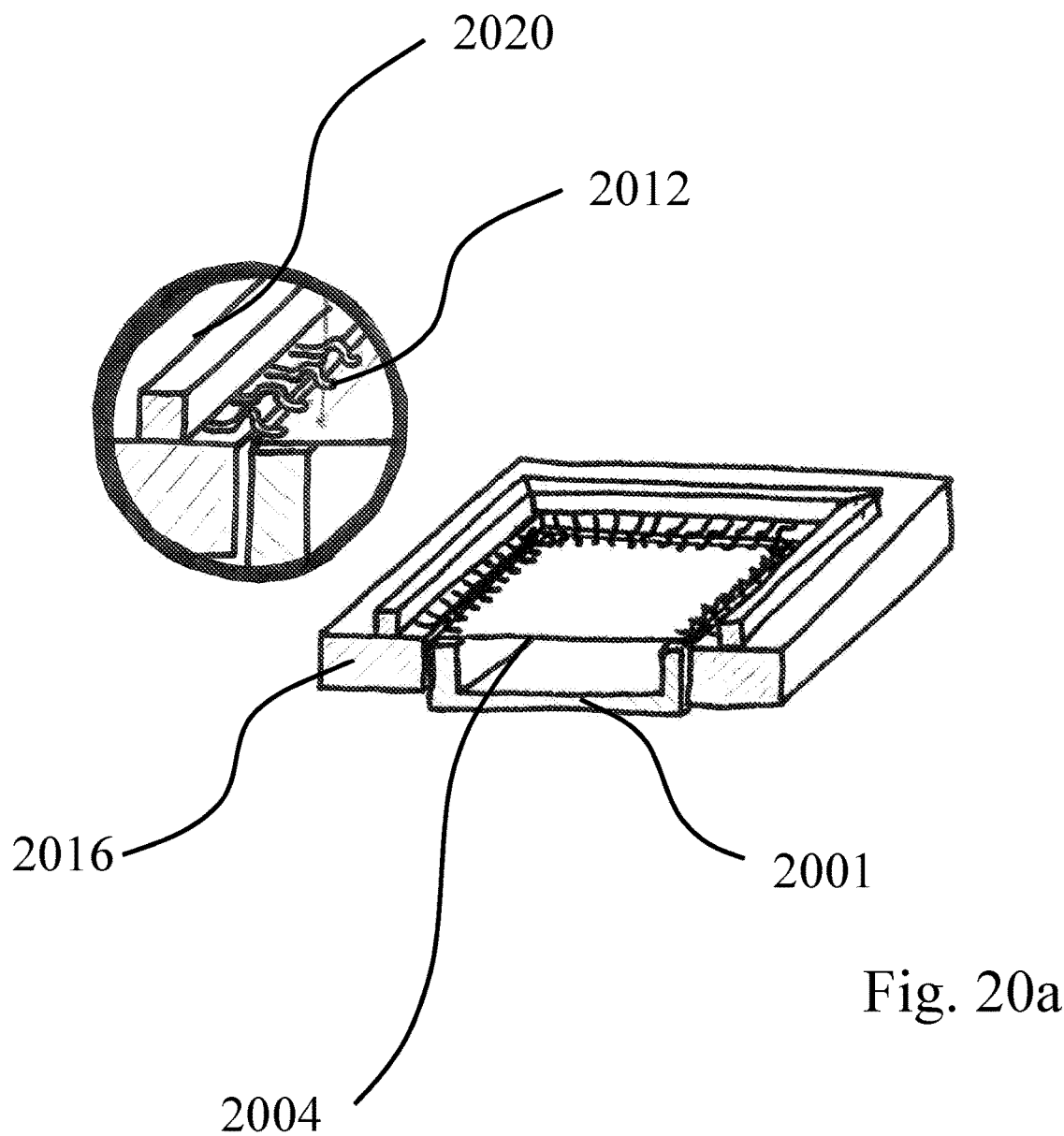

FIGS. 20a and 20b illustrate a further improvement in positioning the foil and the container in close proximity for the welding process. In order to compensate for a certain degree of unevenness of the upper surface of container (2001), and/or thickness variances of foil (2004), frame (2016) is equipped with a number of springs (2012) being formed from short sections of elastic wire, and being mounted between frame (2016) and bracing (2020). The springs are located around the complete circumference of the container, and apply forces that safely press the foil against the container, regardless of minimal variances in the dimensions of container and foil. In an exemplary embodiment, the springs are configured and arranged so that forces are applied every 500 micrometers adjacent the welding seam, and the springs are comb-like extensions to the bracing (2020), or directly integrated in the frame (2016). The individual springs (2012) or the comb-like prongs are configured to have, for example, an elasticity of up to about 1 mm, e.g. about 300 micrometers and to apply, each, a force, for example of up to 10 N, e.g. 1 N.

In yet another exemplary embodiment of the present invention a method comprises the steps of (a) placing a prosthesis in a metal encasement, (b) desorbing the metal components of the encasement, with or without the prosthesis, in a high vacuum chamber, the vacuum, for example in the range of about $10^{-7}$ to 10 mbar, e.g. about $10^{-6}$ mbar, with or without a heating process, for example in the range of about 20° C. to about 400° C., e.g. about 300° C., and (c) hermetically sealing the metal encasement, including the prosthesis. In an alternative embodiment, the aforementioned steps (a) and (b) are performed in reverse order.

The parts as shown in the exemplary embodiments of FIGS. 1 to 10 and 13 to 16 are also described as assemblies when put together in any configuration, in whole or in any partial configuration.

For removal of the prosthesis from the packaging container, the closure must be opened. If a foil is used, a tear strip can be incorporated by deliberately weakening the material at predefined locations by, for example, a line of scoring. This line of scoring or groove can, for example, be applied by stamping, or by directing the laser beam used for welding at the location of the tear strip, and by reducing the power, and/or increasing the speed of movement of the beam, so that the material is engraved but not cut apart.

In an exemplary embodiment of the present invention a system of packaging a prosthesis comprises a prosthesis, a holder and an encasement, the prosthesis including a first custom-shaped portion, the holder including a second custom-shaped portion, the first custom-shaped portion and the second custom-shaped portion provide a form-locking interface, so that, when the holder is operationally positioned inside the encasement and when the prosthesis is operationally positioned in the holder, the holder fixates the prosthesis by means of the form-locking fit in a pre-defined position and orientation inside the encasement, so that the prosthesis surfaces are not in contact with the encasement.

In an exemplary embodiment of the present invention a system of providing a prosthesis for sterile delivery comprises a prosthesis, and a holder the prosthesis including a first custom-shaped portion, the holder including a second custom-shaped portion, the first custom-shaped portion and the second custom-shaped portion provide a form-locking interface, so that, when the prosthesis is operationally positioned in the holder, the holder fixates the prosthesis by means of the form-locking fit in a pre-defined position and orientation with respect to the orientation and position of the holder.

In another exemplary embodiment of the present invention, the holder described in the two directly aforementioned exemplary embodiments is the same holder to be used to fixate the prosthesis inside the encasement and to be used to provide the prosthesis for sterile delivery, so that the treating doctor is able to orient and position the prosthesis by orienting and positioning the holder.

In an exemplary embodiment of the present invention a system of manufacturing and packaging a prosthesis comprises a prosthesis and an encasement, the prosthesis includes a surface conditioned for enhanced hard- and/or soft-tissue integration, the encasement being hermetically sealed to thereby substantially preserve the enhancement for hard- and/or soft-tissue integration of the conditioned surface of the prosthesis, at least a portion of the materials the encasement is made of, are having getter properties to thereby competitively attract impurities enclosed in the hermetically sealed encasement away from the surface of the prosthesis conditioned for enhanced hard- and/or soft-tissue integration.

In the directly aforementioned embodiment, the encasement is for example made of metal. In the directly aforementioned embodiment, the material that is having getter properties is for example made of titanium or a titanium alloy. Alternatively or additionally the getter material is an additional part to be placed inside the encasement. In yet another embodiment the getter material(s) are activated after the encasement is hermetically sealed, for example, by at least by one of the following: exposure to heat, by inductive heat, by mechanical shock and by magnetism. In another embodiment the active getter material(s) are (first) enclosed and are (second) released or exposed to reach the prosthesis, for example, by one of the following: exposure to heat, by inductive heat, by mechanical shock and by magnetism.

In yet another exemplary embodiment of the present invention a system of packaging a prosthesis comprises a prosthesis and a covering, the covering encloses and seals hermetically the prosthesis, the prosthesis is sterile and the materials the covering is made of does not include any organic materials. In the directly aforementioned embodiment, the covering is for example made of metal. In the directly aforementioned embodiment, the covering is for example made titanium or a titanium alloy.

In an exemplary embodiment of the present invention a system of packaging a prosthesis comprises a prosthesis and an encasement, the encasement encloses and seals hermetically the prosthesis, the encasement includes at least one window placed and oriented in the encasement so that the prosthesis is exposed in the encasement to ultraviolet light when the encasement is operationally placed in an ultraviolet light chamber. In the directly aforementioned embodiment, the window is for example made of quartz glass.

In an exemplary embodiment of the present invention a method comprises the steps of hermetically sealing a prosthesis, whether customized or not, in a covering, sterilizing the prosthesis inside the hermetically sealed covering, for example, by at least one of the following sterilization methods: exposure to dry heat, exposure to gamma radiation, exposure to beta radiation, exposure to high-energy ultraviolet light and exposure e-beam radiation, and performing a process to break up hydrocarbons, for example, by at least one of the following mechanisms: a catalytic reaction activated by heat, and photon triggered reaction activated by ultraviolet light. The catalytic reaction can be caused, for example, by one of the following materials: titanium, titanium alloys, titanium oxides zirconia, other metal oxides, and platinum. The term "catalytic reaction" includes a pyrolytic reaction, oxidative reaction, and/or reductive reaction.

In yet another exemplary embodiment of the present invention a system for packaging and sterilizing comprises a prosthesis and an encasement, the encasement encloses the prosthesis, all components of the encasement are made of metal, the encasement is hermetically sealed by welding, and the encasement is labeled sterile.

In yet another exemplary embodiment a hermetically sealed encasement that includes the prosthesis is filled, for example, with at least one of the following: environmental air, inert gas, oxygen, ammoniac, reactive gas mixtures, water (gas), hydrogen peroxide (gas), composed air, and purified air, at any pressure to include increased pressure, pressure of about 1 atmosphere, and vacuum.

In another exemplary embodiment a hermetically sealed encasement that includes the prosthesis is evacuated and filled, for example, with at least one of the following: environmental air, inert gas, oxygen, ammoniac, reactive gas mixtures, composed air, and purified air, at a pressure suitable for plasma or corona discharge, e.g. a range of about 0.1 to about 20 mbar, e.g. about 2 mbar. The discharge is enabled by direct or alternative voltage, e.g. a range of about 20 volts (V) to about 1 kilovolt (kV), e.g. about 400 V, in case of alternative voltage, e.g. a range of about 1 hertz (Hz) to about 4 MHz, e.g. about 40 kHz. Electrodes are placed inside the encasement, for example, the prosthesis and/or the at least a portion of the encasement function(s) as electrode(s). The electric energy is conducted to at least one electrode by an isolating lead through into the encasement or an inductive process. With that, a plasma or corona discharge process may be performed that applies a coating onto a surface of the prosthesis inside the hermetically sealed encasement.

All the aforementioned embodiments and features and methods steps disclosed herein are deemed to be disclosed alone or in any combination, in the disclosed or in reverse order, or in any order as a person skilled in the art would combine and/or order the embodiments, configurations and features and method steps disclosed herein.

Note, it should be understood that one of ordinary skill in the art should understand that the various aspects of the present invention, as explained above, can readily be combined with each other.

The meaning of "CAD" shall include, but shall not be limited to, any and all technology of computer aided design.

The meaning of "CAM" shall include, but shall not be limited to, any and all technology of computer aided manufacturing.

The meaning of "CNC" shall include, but shall not be limited to, any and all technology of computer numerical control as it relates to manufacturing machinery and systems, including but not limited to rapid prototyping devices and systems.

The meaning of "rapid prototyping" shall include, but shall not be limited to, technologies qualified for manufacturing of copies of virtual three-dimensional objects and also technologies qualified for mass customization or the mass production of copies of customized or adapted geometries to the needs of an individual patient. Rapid prototyping in this context shall include, but not be limited to, manufacturing technologies based on the digital data, by a process that includes depositing material, in accordance with the digital data, layer-by-layer in a plurality of layers each constituting a two-dimensional cross section of a solid object having an edge defined by data of the three-dimensional surface, the layers being stacked in a third dimension to form the solid object having a three-dimensional surface defined by the data.

Such rapid prototyping technologies can be directed to actually manufacturing the part of interest, for example, by selective laser sintering or indirect by fabricating first e.g., a resin or wax sample of the part of interest, and second using, for example, "lost-wax" casing to duplicate such sample and fabricate therewith the part of interest. It also includes sintering techniques where the "green" body is printed in response to computerized numerical controlled (CNC) data and sintered it to its final material properties. Sintering in this context includes pressure and heat.

The meaning of "prosthesis" shall include any substantially artificially shaped part of any natural and artificial material.

Whenever the context requires, the word "prosthesis" shall be deemed to include the word "implant" and vice versa.

"3D" shall mean three-dimensional.

The meaning of "imaging", "scan" and "scanning" shall include, but shall not be limited to, any and all technology of acquiring two-dimensional and/or three-dimensional data of physical objects or parts of a human body.

The meaning of clinical "imaging data" shall include, but shall not be limited to, in-vivo and in-vitro processes that result in any anatomical data of the anatomy of a human being. In this context the term data shall include, but shall not be limited to, two-dimensional and three-dimensional data.

The meaning of three-dimensional data shall include, but shall not be limited to, surface (e.g. triangulated data) and volumetric (e.g. voxel) data.

The words used in this specification to describe the various exemplary embodiments of the present invention are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word, itself.

The various embodiments of the present invention and aspects of embodiments of the invention disclosed herein are to be understood not only in the order and context specifically described in this specification, but to include any order and any combination thereof. Whenever the context requires, all words used in the singular number shall be deemed to include the plural and vice versa. Words which import one gender shall be applied to any gender wherever appropriate. Whenever the context requires, all options that are listed with the word "and" shall be deemed to include the world "or" and vice versa, and any combination thereof. The titles of the sections of this specification and the sectioning of the text in separated paragraphs are for convenience of reference only and are not to be considered in construing this specification.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

In the drawings and specification, there have been disclosed embodiments of the present invention, and although specific terms are employed, the terms are used in a descriptive sense only and not for purposes of limitation, the scope of the invention being set forth in the following claims, when attached. The invention has been described in considerable detail with specific reference to the illustrated embodiments. It will be apparent, however, that various modifications and changes can be made within the spirit and scope of the invention as described in the foregoing specification.

The invention claimed is:

1. A holder for holding a prosthesis, the holder comprising:
a first custom-shaped holder portion coupled to a second custom-shaped holder portion to define an implant-receiving portion at a first end of the holder, a gripping portion at a second end of the holder, and a furrow disposed between the implant-receiving portion and the gripping portion,
the implant-receiving portion having an internal surface shaped to grip a custom-shaped corresponding portion of the prosthesis, and an outer surface with a concave curve corresponding to a tooth shape adjacent an implant site for the prosthesis,
the gripping portion having an indent shaped to receive fingers of a user to releasably grip the custom-shaped corresponding portion of the prosthesis, and the holder operable to distribute gripping force around the custom-shaped corresponding portion of the prosthesis for placement of the prosthesis within a patient, and
the furrow being circumferentially narrower than the implant-receiving portion and the gripping portion, and the furrow receives a portion of casing when the holder is packaged.

2. The holder according to claim 1, wherein the holder is operable to grip the prosthesis in a predefined spatial position and orientation with respect to a spatial position and orientation of the holder.

3. The holder according to claim 1, wherein the first custom-shaped holder portion and the second custom-shaped holder portion are joined by a hinge proximate to the second end of the holder.

4. The holder according to claim 1, wherein the first custom-shaped holder portion is a first clamp and the second custom-shaped holder portion is a second clamp, the first clamp and the second clamp configured to provide a clamping mechanism, the holder being operable to position the prosthesis in the holder and release the prosthesis from the holder.

5. The holder according to claim 4, wherein the first clamp includes a first custom-shaped inner portion, wherein the second clamp includes a second custom-shaped inner portion, and the first custom-shaped inner portion and the second custom-shaped inner portion are operable to provide a form-locking interface with the custom-shaped corresponding portion of the prosthesis, so that, when the prosthesis is positioned in the holder, the form-locking interface fixates the prosthesis in the holder.

6. The holder according to claim 1, wherein the holder is operable to insert the prosthesis into a body of the patient without the prosthesis being removed from the holder prior to insertion into the body of the patient.

7. The holder according to claim 1, wherein the first custom-shaped holder portion includes a key feature providing an undercut that provides an interlock with a corresponding inverse feature of the custom-shaped corresponding portion of the prosthesis when the prosthesis is positioned in the holder.

8. The holder according to claim 1, wherein the holder includes a mark allowing a user to handle and insert the prosthesis in a predetermined orientation in a location.

9. The holder according to claim 1, wherein the holder is operable to grip a custom-made dental implant.

10. The holder according to claim 9, wherein the holder includes a mark, marking a vestibular side of the custom-made dental implant.

11. The holder according to claim 10, wherein the holder is operable to grip a custom-shaped preparation post operable to receive a dental crown.

12. The holder according to claim 11, wherein the internal surface includes an inverse shape operable to grip the custom-shaped preparation post and substantially matching a corresponding portion of the custom-shaped preparation post of the custom-made dental implant.

13. The holder according to claim 1, wherein the holder comprises zirconia.

14. The holder according to claim 1, wherein the holder comprises titanium.

15. The holder according to claim 1, wherein the first custom-shaped holder portion includes an orientation notch formed into an outer portion of the implant-receiving portion, and the second custom-shaped holder portion omits the orientation notch.

16. The holder according to claim 3, wherein the hinge connects a first interior surface at the gripping portion of the first custom-shaped holder portion to a second interior surface of the gripping portion of the second custom-shaped holder portion.

* * * * *